US011333612B2

(12) United States Patent
Huang et al.

(10) Patent No.: US 11,333,612 B2
(45) Date of Patent: May 17, 2022

(54) CONNECTORS FOR COLORIMETRIC SENSORS

(71) Applicant: Specific Technologies, LLC, West Palm Beach, CA (US)

(72) Inventors: Richard Shu-Chung Huang, Palo Alto, CA (US); Paul A. Rhodes, Woodside, CA (US); Raymond Anthony Martino, Los Gatos, CA (US)

(73) Assignee: Specific Technologies, LLC, West Palm Beach, FL (US)

( * ) Notice: Subject to any disclaimer, the term of this patent is extended or adjusted under 35 U.S.C. 154(b) by 483 days.

(21) Appl. No.: 15/695,841

(22) Filed: Sep. 5, 2017

(65) Prior Publication Data

US 2018/0180554 A1 Jun. 28, 2018

Related U.S. Application Data

(60) Provisional application No. 62/383,263, filed on Sep. 2, 2016.

(51) Int. Cl.
| | |
|---|---|
| *G01N 21/78* | (2006.01) |
| *G01N 21/01* | (2006.01) |
| *G01N 33/00* | (2006.01) |
| *G01N 33/483* | (2006.01) |
| *G01N 21/77* | (2006.01) |
| *G01N 1/00* | (2006.01) |
| *G01N 1/34* | (2006.01) |

(52) U.S. Cl.
CPC ........... *G01N 21/783* (2013.01); *G01N 21/01* (2013.01); *G01N 33/0031* (2013.01); *G01N 33/0047* (2013.01); *G01N 33/483* (2013.01); *G01N 1/34* (2013.01); *G01N 2001/002* (2013.01); *G01N 2021/0106* (2013.01); *G01N 2021/7796* (2013.01)

(58) Field of Classification Search
CPC ............ G01N 21/783; G01N 33/0031; G01N 33/483; G01N 33/0047; G01N 21/01; G01N 1/34; G01N 2001/002; G01N 2021/0106; G01N 2021/7796
See application file for complete search history.

(56) References Cited

U.S. PATENT DOCUMENTS

| 5,232,839 | A | * | 8/1993 | Eden | ...................... C12M 41/46 435/287.4 |
| 5,518,895 | A | * | 5/1996 | Thorpe | .................. C12M 41/26 435/287.5 |

(Continued)

*Primary Examiner* — Lore R Jarrett
(74) *Attorney, Agent, or Firm* — Nixon Peabody LLP

(57) ABSTRACT

Accordingly, disclosed are various connectors for connecting a colorimetric sensor array to a sample bottle. These connectors allow the colorimetric sensor array to be attached to a sample bottle after autoclaving, and introduce the headspace gas to the colorimetric sensor array at the appropriate time. Examples of these connectors include (1) a needle based connector that punctures the septum of standard bottle to allow gas flow in a chamber with a colorimetric sensor array, (2) a valve based connector that attaches to a sample bottle and when the valve is opened the headspace gas has a path to diffuse to contact a sensor array, and (3) a connector that includes a breakable seal that when broken puts the headspace gas in contact with the colorimetric sensor array.

11 Claims, 30 Drawing Sheets

(56) References Cited

U.S. PATENT DOCUMENTS

| | | | | |
|---|---|---|---|---|
| 5,856,175 | A | * | 1/1999 | Thorpe ................... C12M 41/36 435/287.5 |
| 6,203,529 | B1 | * | 3/2001 | Gabriel ............... A61M 5/3202 604/192 |
| 6,903,823 | B1 | * | 6/2005 | Muller .................. G01N 33/497 356/437 |
| 9,856,446 | B2 | * | 1/2018 | Suslick .................... C12Q 1/10 |
| 2008/0199904 | A1 | * | 8/2008 | Suslick .................. C12M 23/08 435/34 |
| 2009/0296083 | A1 | * | 12/2009 | Saaski .................. G01N 21/552 356/246 |
| 2010/0000960 | A1 | * | 1/2010 | Anderson .......... B65D 51/2807 215/228 |
| 2012/0029440 | A1 | * | 2/2012 | Boyd .................... A61M 5/002 604/192 |
| 2013/0053751 | A1 | * | 2/2013 | Holtham ............... A61M 5/002 604/1 |
| 2013/0303929 | A1 | * | 11/2013 | Martino ................. A61B 5/082 600/532 |
| 2015/0099694 | A1 | * | 4/2015 | Lim ........................ C12Q 1/04 514/2.7 |
| 2019/0183730 | A1 | * | 6/2019 | Lentz .................... A61J 1/2096 |

* cited by examiner

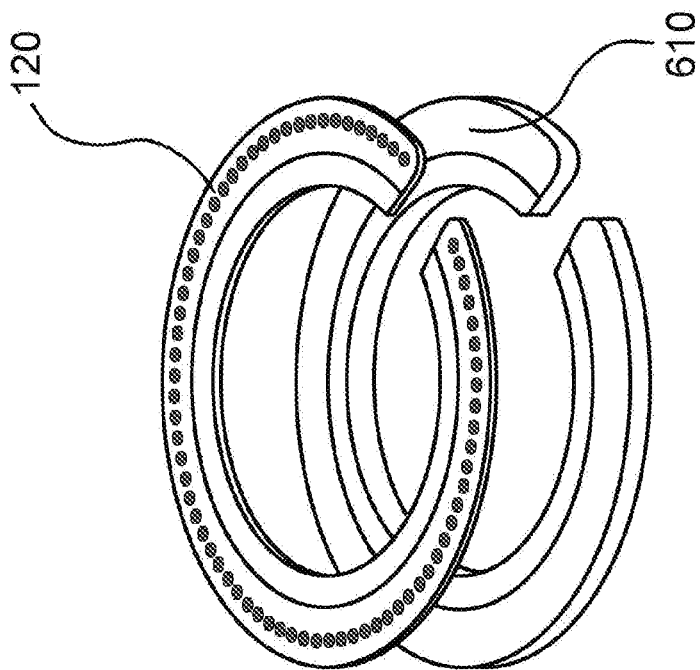
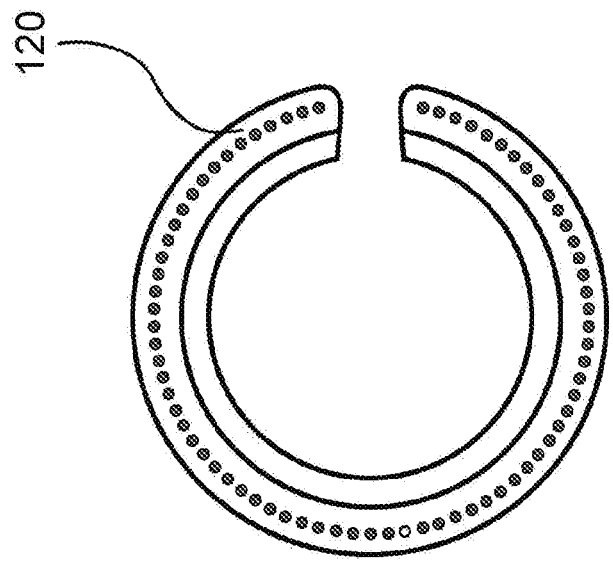
FIG. 6A
FIG. 6B
FIG. 6A-6B

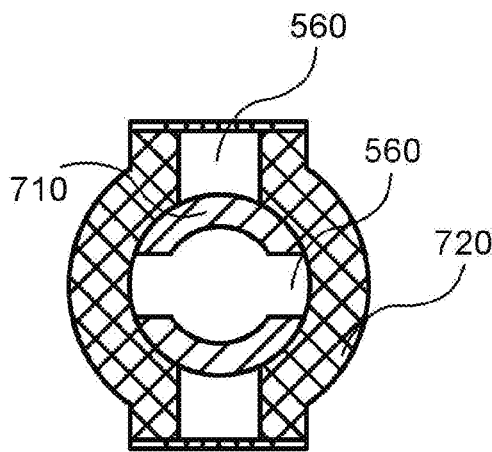
FIG. 8A
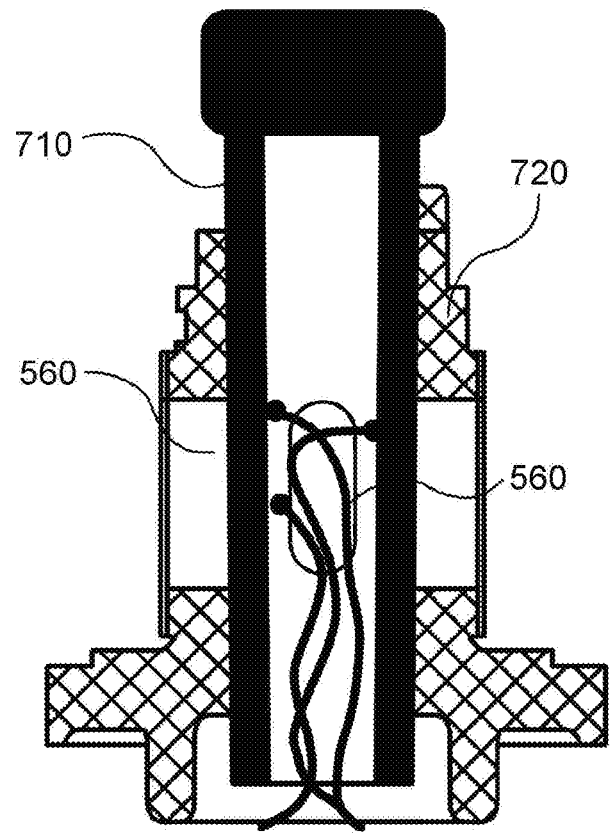
FIG. 8B
FIG. 8A-8B

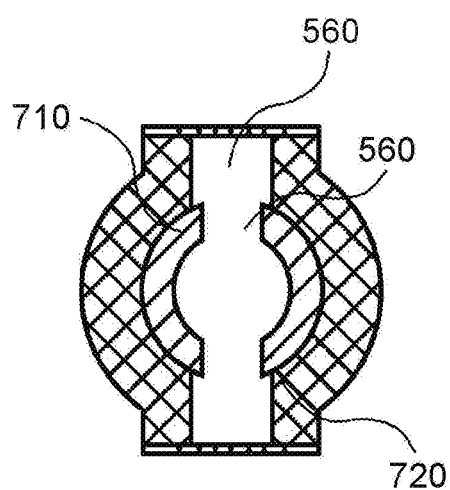
FIG. 9A
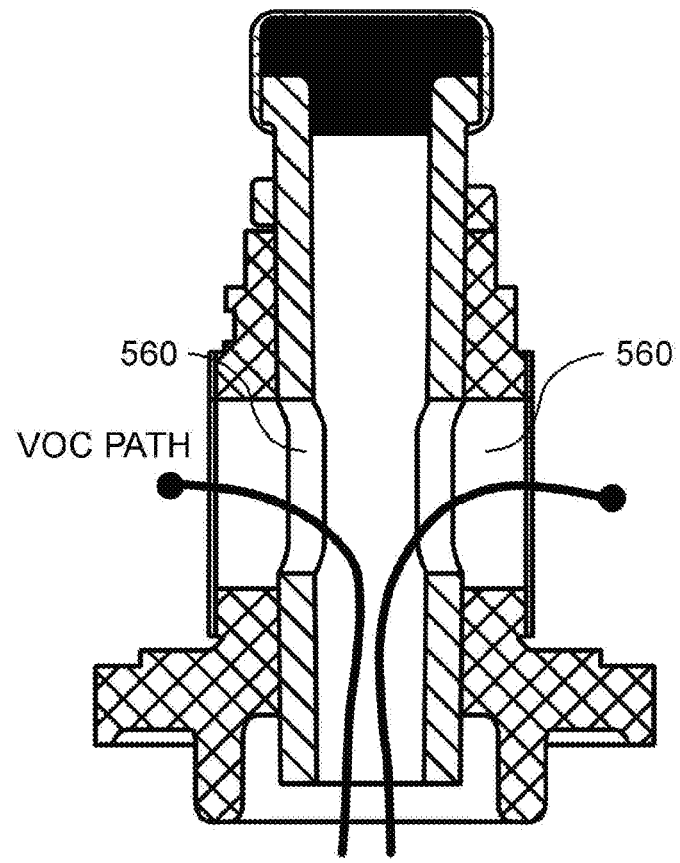
FIG. 9B
FIG. 9A-9B

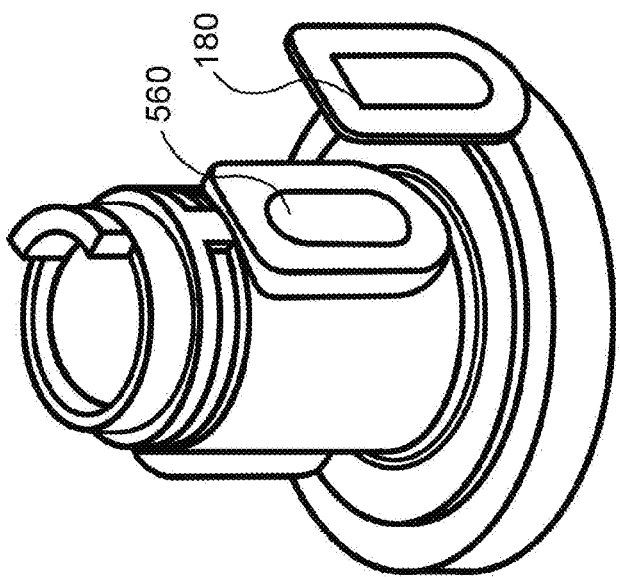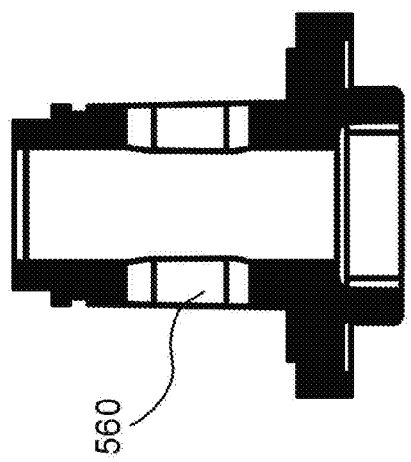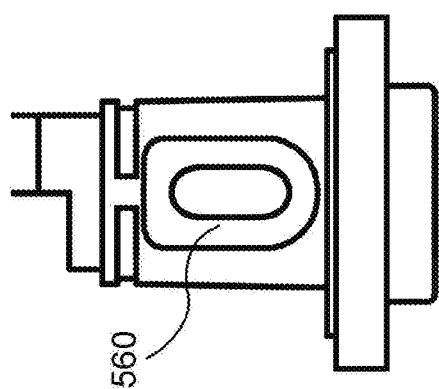
FIG. 10A
FIG. 10B
FIG. 10C
FIG. 10A-10C

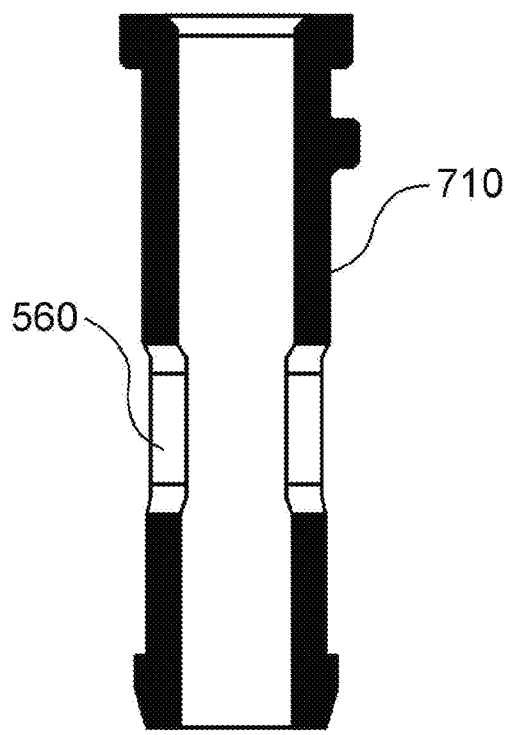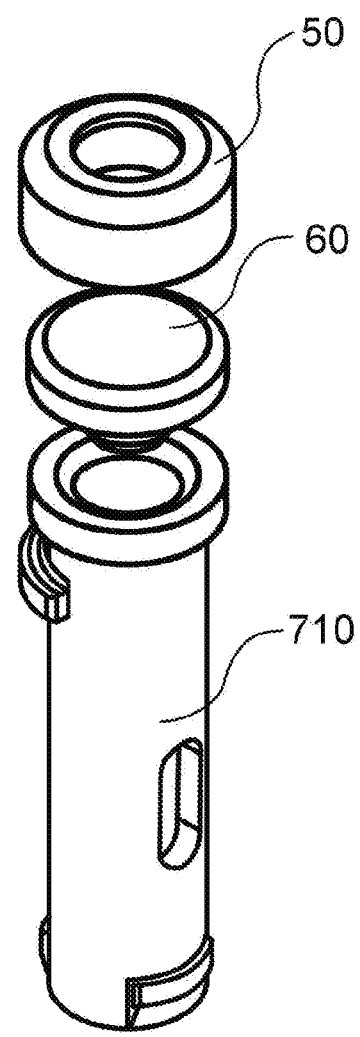
FIG. 11A   FIG. 11B
FIG. 11A-11B

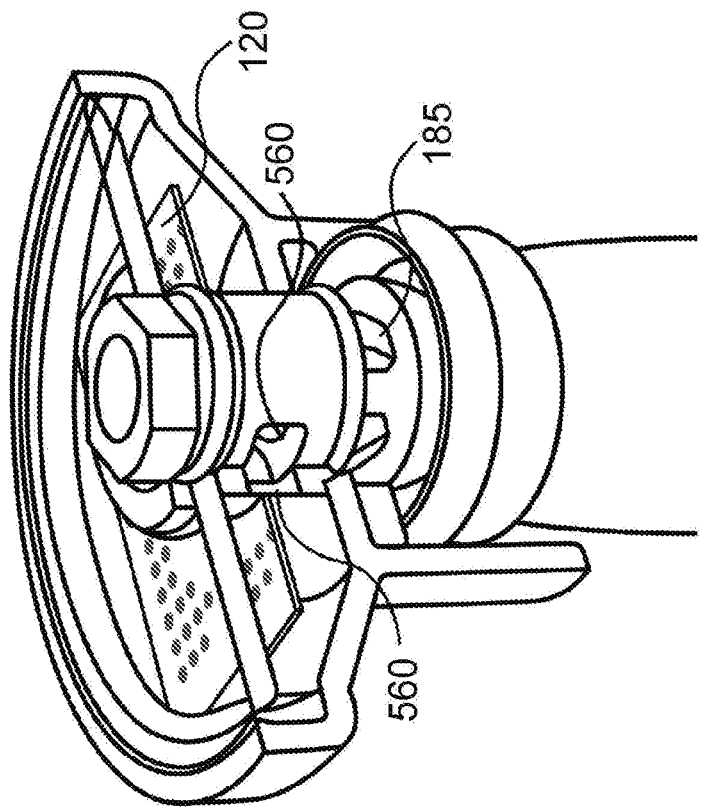
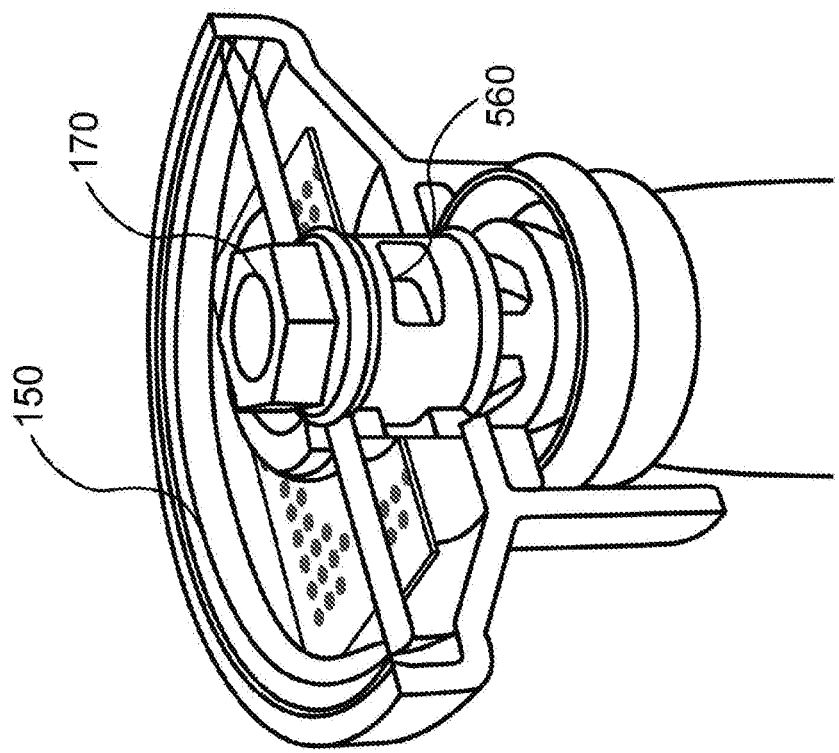
FIG. 12A   FIG. 12B
FIG. 12A-12B

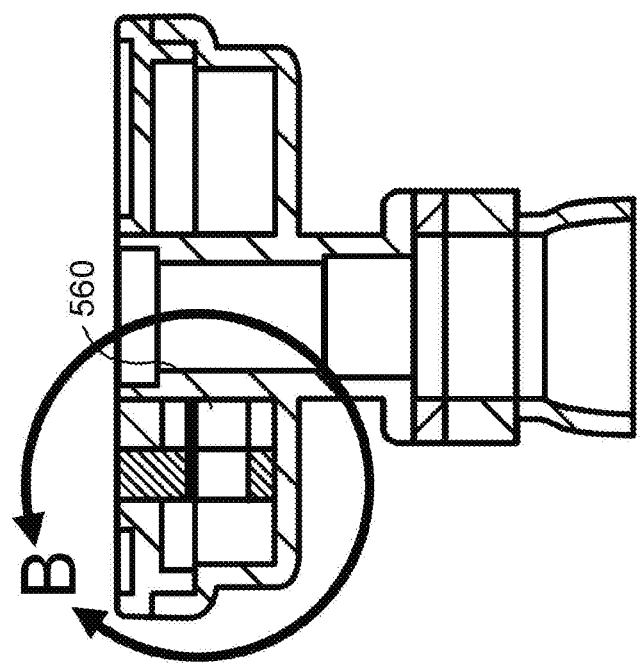
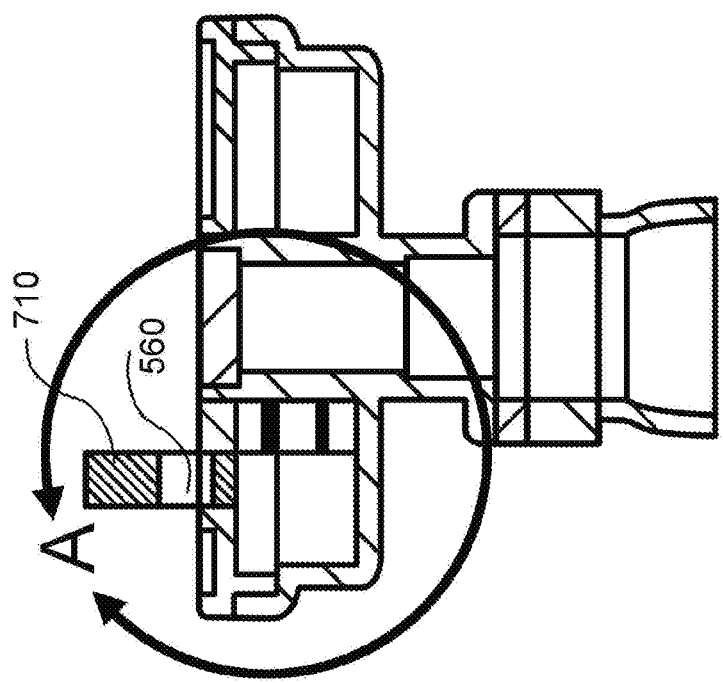
FIG. 15A
FIG. 15B
FIG. 15A-15B

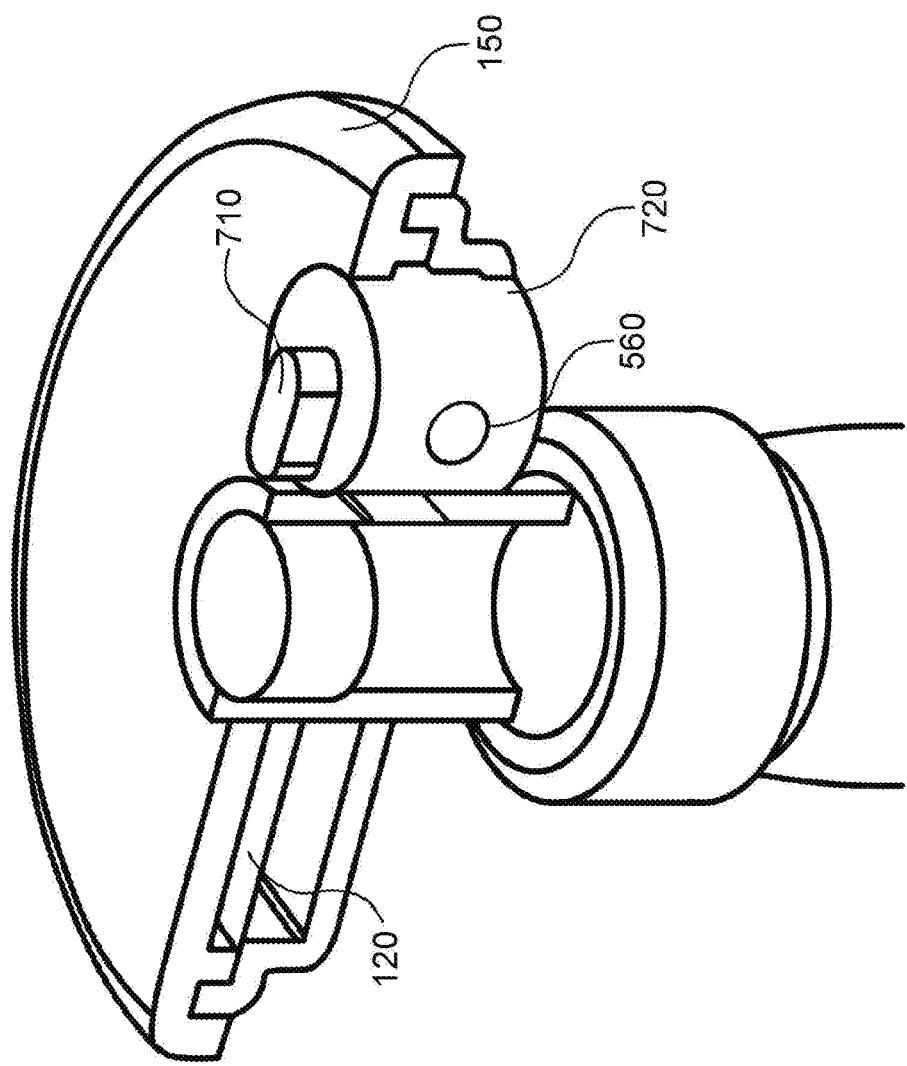

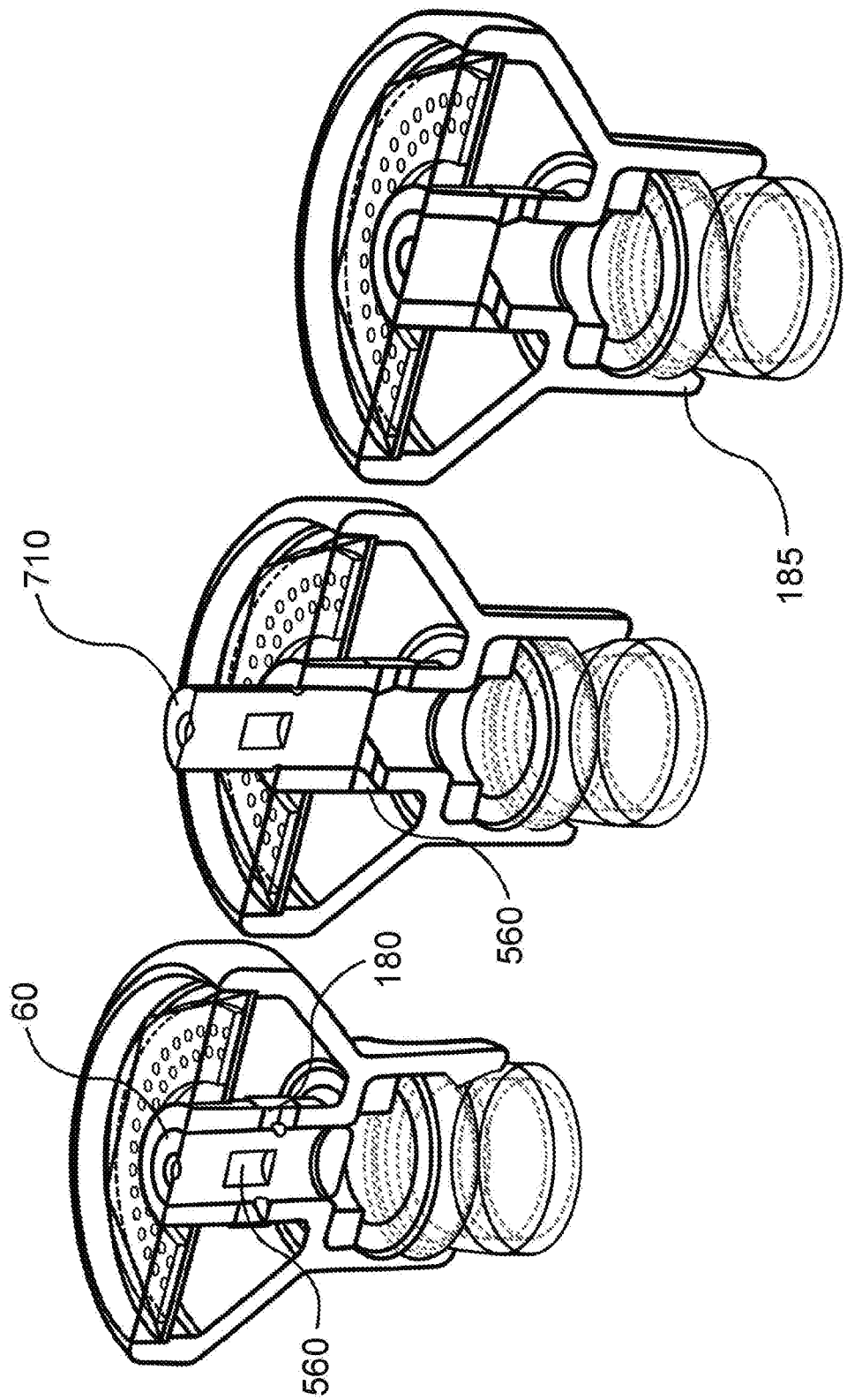

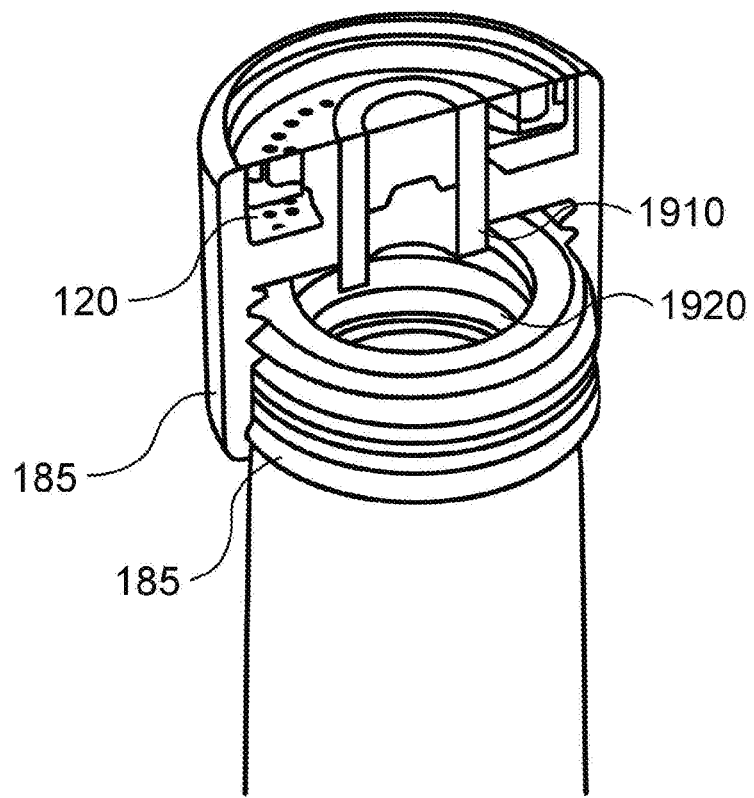
FIG. 19A
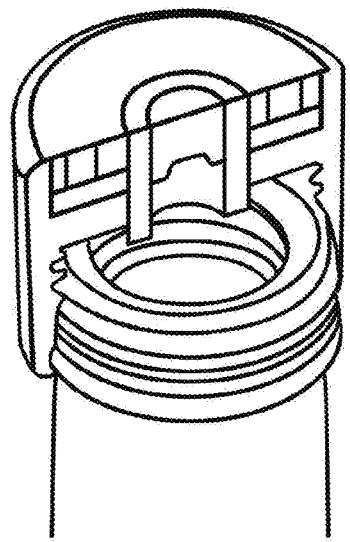
FIG. 19B
FIG. 19A-19B

CONNECTORS FOR COLORIMETRIC SENSORS

FIELD OF THE DISCLOSURE

The present invention is directed to systems and methods for connecting sensor arrays to sample bottles. More particularly, the present disclosure relates to a device, a method, and a system for connecting a colorimetric sensor array to a sample bottle.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

Artificial nose technologies are used to identify foods, bacteria, illnesses in patient samples, and a variety of other applications. Examples of artificial nose technologies including colorimetric sensor arrays that change color in a specific pattern when they contact certain airborne molecules that are emitted by foods, bacteria, and other organic things. The color change pattern on the sensor array can be used as a finger print to identify the source of the airborne modules that contacted the colorimetric sensor array.

Colorimetric sensors include one or more materials that undergo a change in spectral properties upon exposure to an appropriate change in the environment of the sensor. The change in spectral properties may include a change in the absorbance, fluorescence and/or phosphorescence of electromagnetic radiation, including ultraviolet, visible and/or infrared radiation.

Many colorimetric sensors include chemoresponsive dyes that change color in response to volatile organic compounds ("VOCs") (or other compounds) that evaporate from urine or blood samples, or from foods. VOCs are organic compounds that easily become vapors or gases. Along with carbon, they contain hydrogen, oxygen, fluorine, chlorine, bromine, sulfur, nitrogen or other compounds. Blood and urine samples, for instance, contain VOCs that are, among other things, the byproducts of metabolism of cells in the body (e.g. cancer cells) or the byproducts of metabolism bacteria (e.g. pneumonia or other infections).

Samples that include, for instance, microorganisms that produce VOCs will off gas VOCs at various rates over time. For instance, if a blood sample is cultured that includes an infectious bacteria, the bacteria will grow over time and excrete various compounds, some of which will be off gassed as VOCs. If the sample is contained in a vial, the VOCs will evaporate into the head space gas, or the space surrounding the sample. When the head space gas is brought into contact with a colorimetric sensor array that that includes chemoresponsive dyes or other artificial nose technologies, the colorimetric sensor array will change color in a pattern that changes over time as the VOC profile contacting the array changes.

The color change pattern may be detected by an optical or other radiation, spectroscopic, transmission or reflectance detector and the pattern may be correlated to the presence of certain VOCs in certain concentrations. Those VOC concentration profiles may be associated with certain diseases, infections, or other maladies, in some examples.

For instance, culturing a sample including a microorganism (e.g., a species of bacteria) in the presence of a colorimetric sensor array exposes sensors in the colorimetric sensor array to volatile organic compounds produced by the microorganism. U.S. Patent Publication No. 2008/0199904 to Suslick et al., U.S. Patent Publication No. 2010/0166604 to Lim et al., and Carey et al., "Rapid Identification of Bacteria with a Disposable Colorimetric Sensing Array," J. Am. Chem. Soc. 2011, 133, 7571-7576, all of which are incorporated by reference herein, describe an example of an application of colorimetric sensor arrays—identification of bacteria from volatiles they produce using colorimetric sensor arrays. In that example, response of the sensors in the colorimetric sensor array to the volatile organic compounds yields a strain-specific temporal or static color response pattern, allowing the microorganism to be identified by comparison of the color response pattern with color response patterns for known strains. Comparison may be achieved, for example, visually or automatically.

SUMMARY OF THE DISCLOSURE

Colorimetric sensor arrays are quite sensitive to contamination and must be kept in an inert environment that does not include VOCs that are reactive to the array prior to introduction to the headspace gas from a sample. Additionally, colorimetric sensor arrays are destroyed by the high temperature of autoclaving and other sterilization processes, and therefore developing mechanical systems for attaching the sensor arrays to sample bottles is challenging.

Accordingly, disclosed are various connectors for connecting a colorimetric sensor array to a sample bottle. These connectors allow the colorimetric sensor array to be attached to a sample bottle after autoclaving (in some examples), and introduce the headspace gas to the colorimetric sensor array at the appropriate time. Examples of these connectors include (1) a needle based connector that punctures the septum of a standard bottle to allow gas flow in a chamber with a colorimetric sensor array, (2) a valve based connector that attaches to a sample bottle and when the valve is opened the headspace gas has a path to diffuse to contact a sensor array, (3) a connector that includes a breakable seal that when broken puts the headspace gas in contact with the sensor array, and (4) a bottle with a seal over a portion of the sample vial that includes a filter (that when the seal is removed allows headspace gas to diffuse out) that when removed, allows a connector to be attached that puts the headspace gas in contact with the colorimetric sensor array.

In an aspect of the present disclosure, a connector for introducing gaseous particles from a sample bottle to a colorimetric sensor array is disclosed. The connector includes a compartment; a sensor array inside the compartment, the sensor array comprising at least two chemoresponsive dyes; and a needle with a channel connected the compartment, the channel in gaseous communication with the compartment.

The compartment may include an at least partially transparent window and the sensor array is positioned with the at least two chemoresponsive dyes facing the at least partially transparent window.

The connector may further include a housing forming a wall on three sides of the needle and a peel away seal covering the fourth side of the needle to form a sterile cavity for the needle.

The sensor array may be a colorimetric sensor array.

The connector may further include a filter positioned in gaseous communication with the channel of the needle.

The filter may include a hydrophobic filter.

The filter may include a biofilter with pore size of 0.2 um.

A method of using the connector, wherein the needle is plunged through a septum of a sample bottle.

The connector may be clipped into the cap of the sample bottle with a retainer attached to the connector.

In yet another aspect of the present disclosure, a connector for introducing gaseous particles from a sample bottle to a colorimetric sensor array is disclosed. The connector includes a compartment; a sensor array inside the compartment; a valve comprising at least one valve port in gaseous communication with the compartment; an actuator connected to the valve; and a retainer.

The valve may further include an inner valve with a valve port and an outer valve with a valve port.

The actuator may include a knob.

The retainer may include a screw assembly.

The retainer may include a clipping mechanism.

The sensor array may include a disc shaped sensor array.

The inner and outer valve may be posited and constructed to allow relative rotation between the inner and outer valve.

In yet another aspect of the present disclosure, a method of introducing gaseous particles from a sample bottle to a colorimetric sensor array is disclosed. The method includes: providing the connector as disclosed herein; attaching the connector to a sample bottle; and manipulating the actuator and thereby opening the valve to allow gas to flow from the sample bottle to the sensor array.

The valves may include an inner valve with an inner valve port and an outer valve with an outer valve port.

The opening the valve may include lining up the inner valve port and outer valve port.

In yet another aspect of the present disclosure, a method of assembling a connector is disclosed. The method includes: attaching the retainer to a sample bottle, the retainer being attached to a valve; autoclaving the retainer, the sample bottle and valve assembly; attaching a colorimetric sensor to the valve; and sealing a compartment onto the valve.

In another aspect of the present method of using a connector, the method including; providing a connector including a compartment with a colorimetric sensor array, the connector attached to a sample bottle with a sample inside; removing an obstruction from a flow path from the sample bottle gas headspace to the colorimetric sensor array; detecting a change in the colorimetric sensor array after removing the obstruction; and processing the change in the colorimetric sensor array to output an indication of the sample.

A connector for introducing gaseous particles from a sample bottle to a colorimetric sensor array, the connector including: a compartment; a sensor array inside the compartment; a seal blocking a gaseous communication channel between the compartment and a sample bottle; a retainer; and a protrusion positioned and configured to be movable to contact and break the seal.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6A depicts, according to various examples, a perspective view of a disc shaped colorimetric sensor array;

FIG. 6B depicts, according to various examples, a top view of a ring shaped colorimetric sensor array;

FIG. 8A depicts, according to various examples, a radial cross sectional view of a valve for a connector;

FIG. 8B depicts, according to various examples, a longitudinal cross sectional view of a valve for a connector;

FIG. 9A depicts, according to various examples, a radial cross sectional view of a valve for a connector;

FIG. 9B depicts, according to various examples, a longitudinal cross sectional view of a valve for a connector;

FIG. 10A depicts, according to various examples, a side view of a valve for a connector;

FIG. 10B depicts, according to various examples, a longitudinal cross sectional view of a valve for a connector;

FIG. 10C depicts, according to various examples, perspective view of a valve for a connector;

FIG. 11A depicts, according to various examples, a longitudinal cross sectional view of a valve for a connector;

FIG. 11B depicts, according to various examples, a perspective view of a valve for a connector;

FIG. 12A depicts, according to various examples, a perspective view of a valve based connector attached to a sample bottle;

FIG. 12B depicts, according to various examples, a perspective view of a valve based connector attached to a sample bottle;

FIG. 15A depicts, according to various examples, a longitudinal cross sectional view of a valve based connector attached to a sample bottle;

FIG. 15B depicts, according to various examples, a longitudinal cross sectional view of a valve based connector attached to a sample bottle;

FIG. 16 depicts, according to various examples, a perspective cross sectional view of a valve based connector attached to a sample bottle;

FIGS. 17A-17C depict, according to various examples, perspective cross sectional views of a valve based connector attached to a sample bottle;

FIGS. 19A-19B depict, according to various examples, perspective cross sectional views of a seal breaking based connector attached to a sample bottle;

Figure 1:
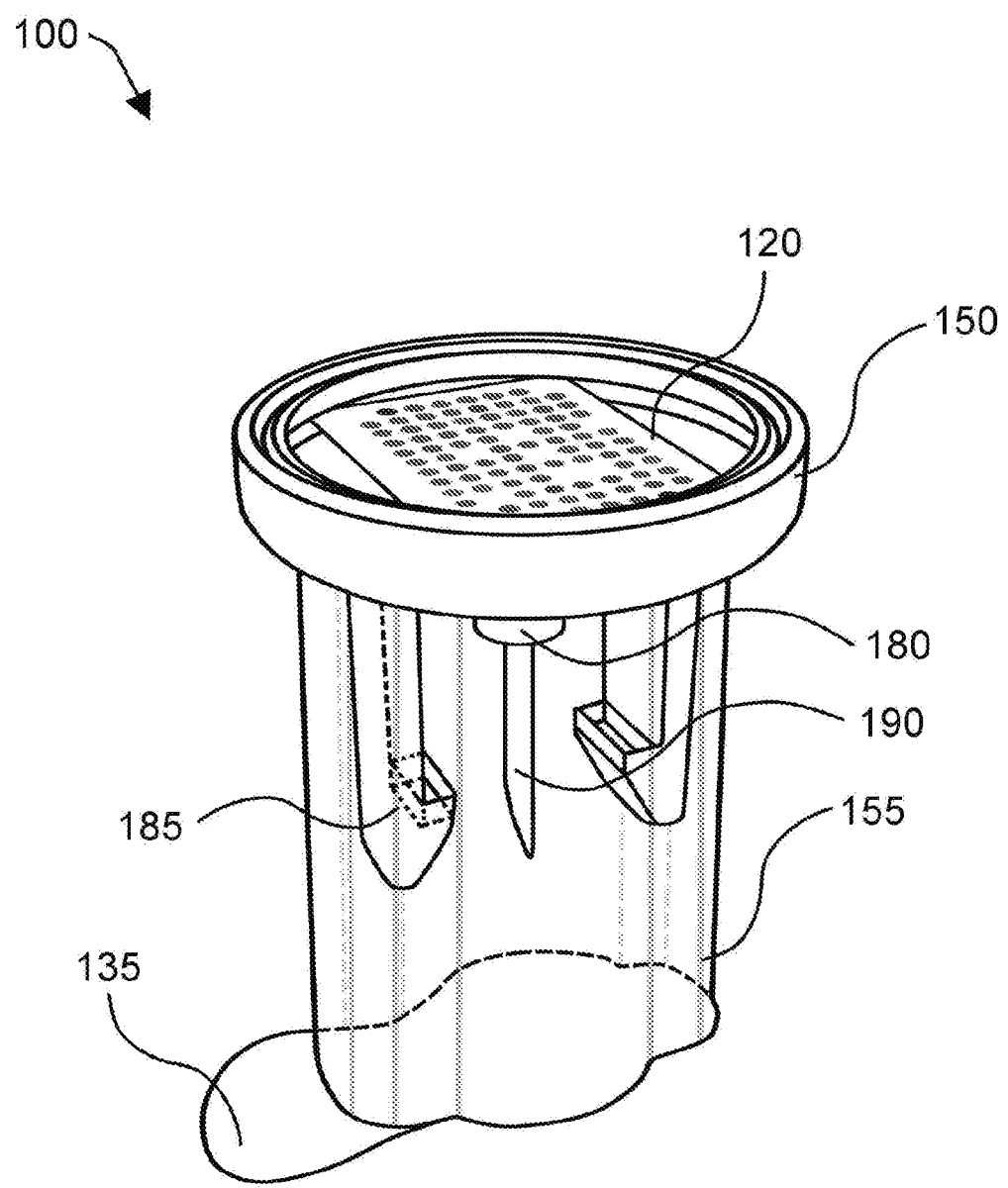
FIG. 1 depicts, according to various examples, a perspective view of a needle based connector.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE PRESENT DISCLOSURE

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Accordingly, disclosed are various connectors for connecting a colorimetric sensor array to a sample bottle. These connectors allow the colorimetric sensor array to be attached to a sample bottle after autoclaving (in some examples), and introduce the headspace gas to a colorimetric sensor array at the appropriate time. Examples of these connectors include (1) a needle based connector that punctures the septum of standard bottle to allow gas flow in a chamber with a colorimetric sensor array, (2) a valve based connector that attaches to a sample bottle and when the valve is opened the headspace gas has a path to diffuse to contact a sensor array, (3) a connector that includes a breakable seal that when broken puts the headspace gas in contact with the colorimetric sensor array, and (4) a bottle with a seal over a portion of the sample vial that includes a filter (that when the seal is removed allows headspace gas to diffuse out) that when removed, allows a connector to be attached that puts the headspace gas in contact with the colorimetric sensor array.

The connectors may include a compartment with a colorimetric sensor array that is separated by a filter from a sample container. The filter may be a hydrophobic filter that is only permeable to gasses and thereby allow the headspace gas to pass through to contact the colorimetric sensor array while preventing the sample medium, any microorganisms, and other material in the sample bottle. The connector also includes a seal that prior to introduction of the headspace gas to the colorimetric sensor, seals the compartment that includes the colorimetric sensor array to prevent contaminants or the headspace gas from prematurely contacting or contaminating the colorimetric sensor array. The connector also includes a retainer that attaches the connector to the sample bottle to provide an airtight seal between the bottle and connector.

Once the headspace gas is ready to be introduced to the array, the seal or other barrier is broken, opened (e.g. valve), punctured, or otherwise removed and the headspace gas will diffuse through the conduits of the connector to the compartment that holds the colorimetric sensor array. Then, a detector may detect the changes on the colorimetric sensor array through the compartment, which may have a transparent face that allows light to pass and reflect from the dyes on the array. As disclosed herein, the seal or other barrier may be broken or removed in a variety of ways, and the connector may be attached to the sample bottle in a variety of ways.

Colorimetric Sensor Arrays

A colorimetric sensor is a sensor that includes one or more materials that undergo a change in spectral properties upon exposure to an appropriate change in the environment of the sensor. The change in spectral properties may include a change in the absorbance, fluorescence and/or phosphorescence of electromagnetic radiation, including ultraviolet, visible and/or infrared radiation.

Artificial noses based on colorimetric sensor arrays are capable of detecting VOCs at low concentrations and a high degree of accuracy. Colorimetric sensor arrays 120 may detect volatile organic compounds by reacting with the compounds and changing color based on the amount and type compounds exposed to the array 120 (as shown in, e.g., FIG. 1). The resulting pattern of color changes comprises a high-dimensional fingerprint which enables the identification of complex mixtures, including disease signatures in exhaled breath and in sealed assays.

Examples of sensor arrays are described in, for example, U.S. Pat. No. 6,368,558, issued on Apr. 9, 2002, titled Colorimetric Artificial Nose Having an Array of Dyes and Method for Artificial Olfaction, and Lim et al, An optoelectronic nose for the detection of toxic gases. Nature Chemistry, 10.1038, 564-567, 2009, both of which are incorporated by reference herein in their entirety.

Compartment

The colorimetric sensor arrays may be contained within a compartment of the connector that is separated from a sample in a bottle by a filter and initially a seal or other barrier. The compartment may include various conduits designed to be able to connect the headspace gas from the sample bottle to the portion of the compartment that includes the colorimetric sensor array. In some examples, most or the rest of the compartment except for the conduit will be not permeable to gas and sealed. The compartment may include a transparent or other window for allowing the colorimetric sensor array pattern to be detected by a detector. In some examples, the detector will detect other wavelengths that are permeable to the compartment material that are not light waves. In some examples, the detector may be external to the compartment or inside the compartment.

Filters

A connector may also include a filter. The filter may screen out liquid and only allow gasses to pass through to contact the sensor array or may filter out microbes as well or alternatively. In some examples, a combination of filters will be utilized that contain a liquid filter and a microbe biofilter. In some examples, the filter may only allow VOCs to pass through, and may be filter that allows smaller molecules that are as small as VOCs to pass.

Filters for filtering out liquids may include a hydrophobic membrane that is only permeable to gasses. For instance, fluorinated polymers (PTFE, PVDF, and expanded PTFE) may be used or polypropylene and polyethersulfone. For the biofilter purpose, the connector may include either a hydrophilic or hydrophobic membrane, but have an average porosity of <0.45 um, and in some cases less than 0.22 um or 0.2 um.

The thickness of various filters may be 130 microns for PTFE and PVDF or 0.5 mm-1.5 mm for expanded PTFE. Materials such as this may be obtained from manufacturers such as Pall, Gore, and Steriltech.

Seal or Other Barrier

The connector may include a seal or other barrier at various portions that maintains a sterile cavity in the compartment prior to introduction of the headspace gas to the colorimetric sensor array. The seal may be a peel away seal that blocks a portion of the connector prior to connecting to the sample bottle. In other examples, the seal may be a valve that is opened by actuation or manipulation of a component on the connector. In some examples the seal could be cork or plug like structure. In some examples, the seal may be a metal foil or other structure that may be broken by an internal mechanism within the connector.

Retainer

In some examples, the connector may include a retainer or device to attach the connector to the sample bottle. For instance, in some examples the retainer may be a clip on, in which case the seal with the bottle will use a different portion. In some examples, the retainer may be a screw and thread system that may form a seal in combination with a gasket. In other examples, the retainer will be a prefabricated portion that permanently attaches the connector to the sample bottle, and may be fabricated all together.

Sample Bottle

Figures 2A, 2B:
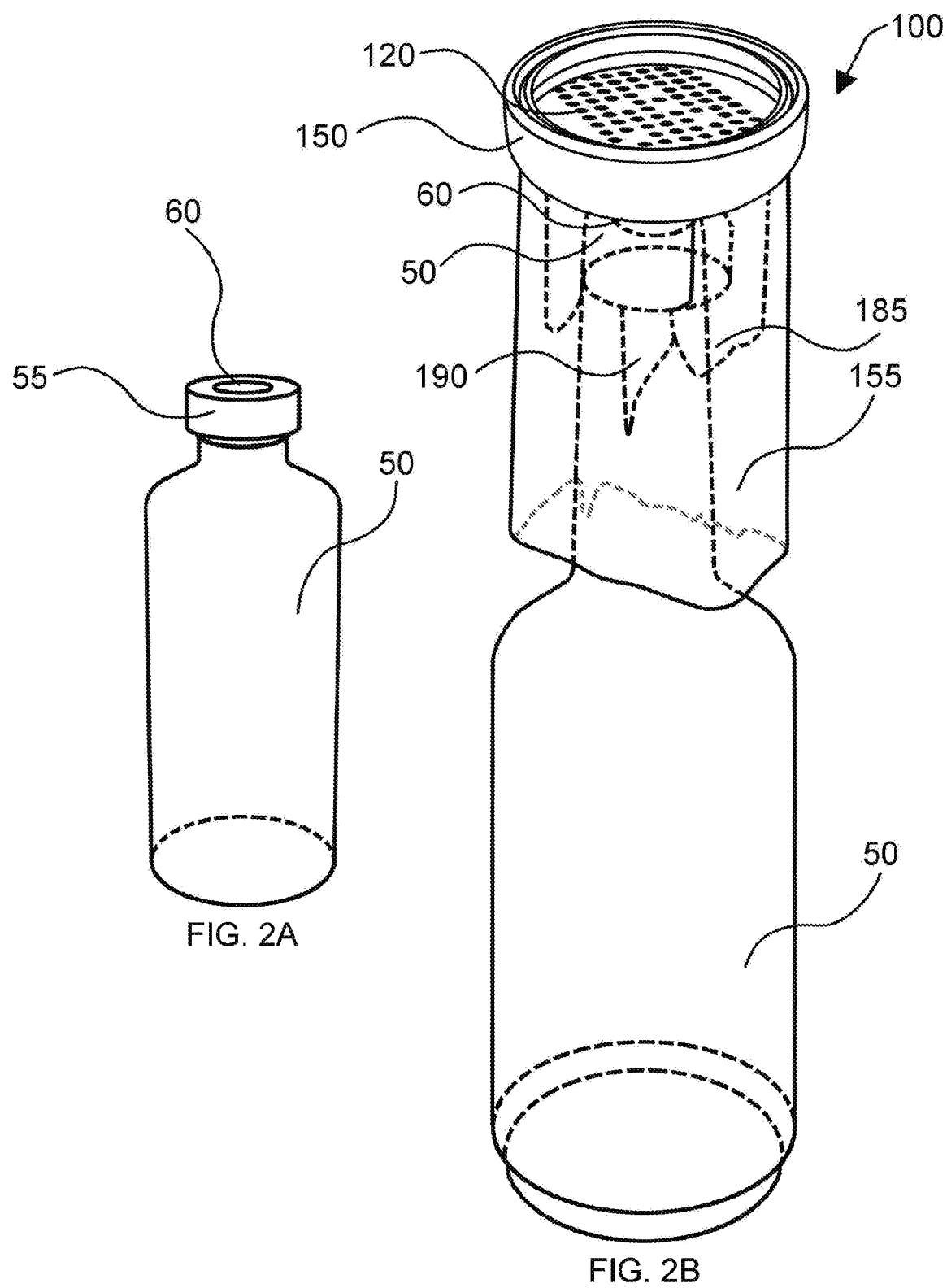
FIG. 2A depicts, according to various examples, a perspective view of a standard sample bottle.
FIG. 2B depicts, according to various examples, a perspective view of a needle based connector inserted in a standard sample bottle.

Sample bottles may come in a variety of forms. For instance, FIG. 2A illustrates a sample bottle may be a conventional sample bottle 50 that includes a cap 50 that seals the opening to the bottle 50 and a septum 60 so that a clinician may use a needle to deposit a sample inside the bottle 50. In some examples, the sample bottle 50 may contain various types of growth media, or may contain only a sample such as a blood, urine, or breath samples. In some examples, the sample bottle may contain a substrate for applying a sample to allow the sample to off gas into the bottle. For instance, for a urine sample the bottle may contain an absorbent substrate to apply the urine sample.

While some examples will include conventional bottles, in other examples customize bottles may be manufactured that accommodate the retainers of the connectors or are integrated with the connector. Accordingly, various types and configurations of sample bottles are disclosed, and the disclosure is not limited to the examples provided.

Manufacturing and Sterilization

Various methods and timing for manufacturing and sterilization of the bottle connector system may be implemented. Many different methods of sterilization may be utilized including for instance, autoclaving, gamma, electron beam, x-ray, and others. For instance, as mentioned, some of the systems will integrate with conventional bottles, and accordingly each can be separately sterilized. In other examples, the connector will be integrated with the bottle or a custom bottle at some point in the manufacturing stage and potentially sterilized together. For these examples, the connector may include different portions that are sterilized separately or added after autoclaving (which is a very high temperature).

For instance, in some examples a portion of the connector that does not include the colorimetric sensor array (which cannot withstand autoclaving temperatures) will be sterilized. Then the colorimetric sensor array can be added and a cap or other cover to form a compartment around the colorimetric sensor array may be added to seal off the colorimetric sensor array compartment in the connector.

Methods

The connector may be utilized to expose the colorimetric sensor array to VOCs or other volatile compounds in the sample bottles according to various methods. For instance, in some examples, a sample will be added to the bottle, and the VOCs off gassed from the bottle will have an immediate path to diffuse and contact the colorimetric sensor array. In other examples, after the sample is applied or deposited in the bottle, the user may need to perform some action to open the path from the bottle headspace to the compartment containing the colorimetric sensor array. This may include turning a valve, breaking or peeling off a seal, unscrewing a cap, or a combination or other methods.

Then once the contact of the headspace gas or other off gas from the sample has begun, a detector may detect changes in the colorimetric sensor array. Accordingly, this can be utilized to determine information about the sample.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Needle Based Connectors

FIG. 1 illustrates an example of a connector 100 as disclosed herein. For instance, the connector 100 disclosed in FIG. 1 may be attached to a standard or conventional bottle (as shown in, e.g., FIG. 2). The connector 100 may include a top portion and a bottom portion. The top portion may be configured to connect with a compartment 150. The bottom portion may be configured to connect with a seal 135. In this example, the seal 135 may be removed from the bottom portion of the connector, which will result in a housing 155 being exposed to ambient air. The connector 100 may include a needle 190 that is configured to protrude from the top portion and be further configured to be inserted into a standard bottle 50 or other bottle with a septum 60 as illustrated in FIGS. 2A-2B. The septum 60 may be a rubber or elastic septum, or other suitable septum 60.

Referring to FIGS. 1 and 2A-2B concurrently, the connector 100 may be pushed down so that the retainers 185 clip onto the underside of a standard cap 50. This is useful to retain the connector 100 in position and prevent the connector 100 from being pushed off in case pressure builds up. In this example, because the septum 60 is pierced with a needle, a seal is formed between the septum 60 and the needle 190 and a separate seal to the bottle is not necessary. Other retainers could be utilized, for instance, the retainer could screw onto the threads of the bottle 50 after the cap 55 is removed.

The connector 100 in this case may include a colorimetric sensor array 120 ("CSA") that is contained in a compartment 150 with a transparent window on top of the calorimetric sensor array 120 to allow light to pass through. Accordingly, once attached, the connector 100 may be placed in an incubator or rack, and a detector (not shown) can monitor the colorimetric sensor array 120 through the window in the compartment 150.

As illustrated the needle 190 may include a metal (FIG. 1) or plastic (FIG. 2) needle. Different sized or multiple needles 190 could be used. The larger the cross-sectional area of the passageway inside the needle 190 the faster diffusion of the headspace gas from the sample bottle 50 to the compartment with the CSA. However, the larger the needle 190 the more likely the seal or septum 60 may be comprised after one usage. Additionally, the shorter the passageway length the faster the diffusion of gases. In some cases, the detector response may need to be calibrated to the needle size, as the time response of the VOCs may be dependent on the diffusion rate. In many examples a filter and/or biofilter may be incorporated in the path between the opening in the bottom of the needle 190 and the opening to the compartment in the connector 100. In an embodiment of the present disclosure, the needle 190 may further include any other needle types necessary to carry out the procedure described herein.

This example is quite advantageous because it allows the connector to be attached to a multitude of already existing bottles and does not require special manufacturing steps. However, this example does require special handling and execution instructions by the clinician or technician.

Figure 3:
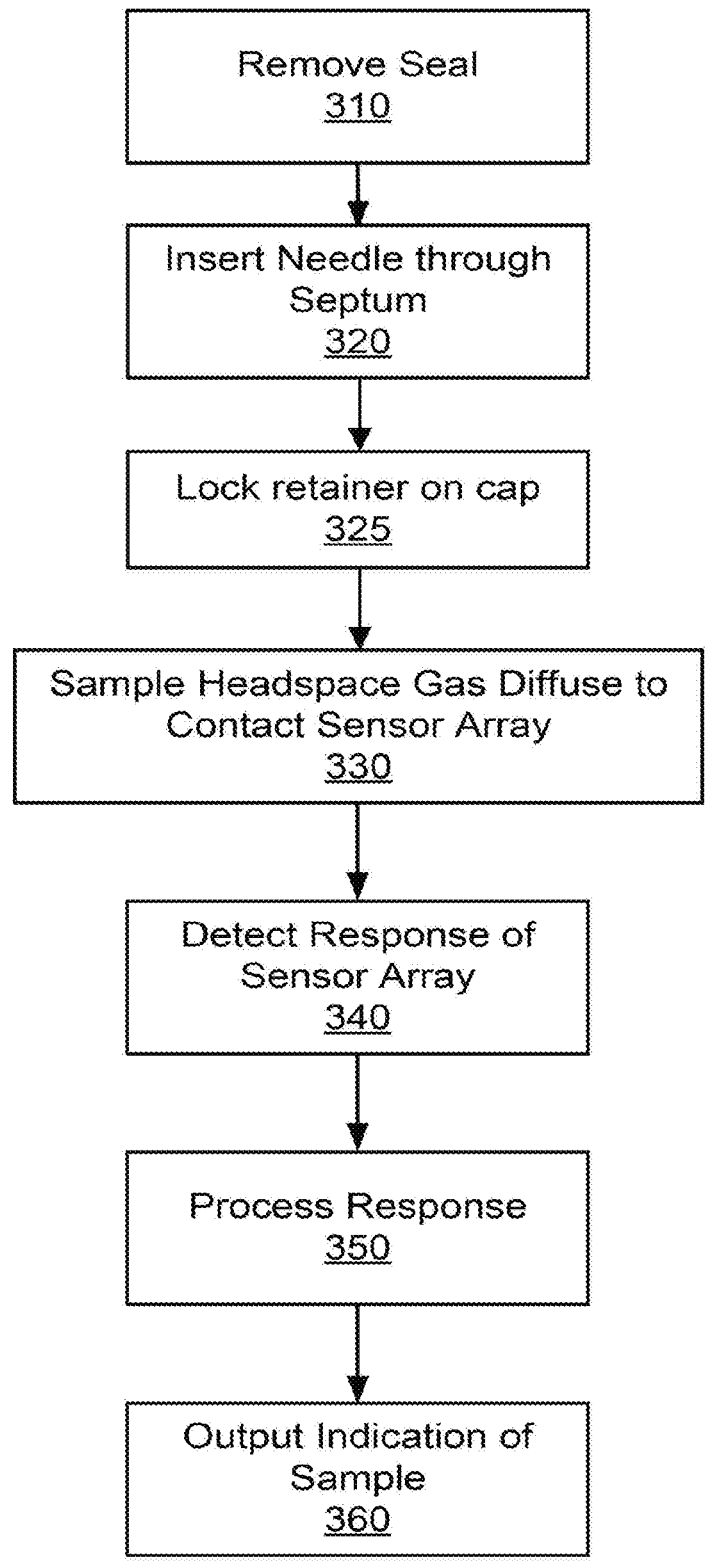
FIG. 3 depicts, according to various examples, a flow chart illustrating a method of using a connector.

FIG. 3 illustrates an example of a method of utilizing a needle based connector 100 in accordance with the principles of the present disclosure. For instance, the method includes removing a seal to expose the needle 190 (Step 310), and then inserting the needle through the septum (Step 320). Then a user may lock the retainer onto the cap (Step 325). This may be performed by pushing down the connector 120 until the wings or tabs clip over the edges of the cap 55, or in other examples, may include a press or push fit around the cap 55, a screw on or other connection mechanism.

Then, the technician (or another user) will allow the sample headspace gas to diffuse to contact the sensor array (Step 330). While this is happening, a detector will be detecting the response of the sensor array (Step 340). Then, a control system may process the response of the detector (Step 350). In some examples, the control system may include different processing criteria based on the model of the connector 100. For instance, each connector 100 may include different diffusion rates, transmission characteristics through the window of the compartment 150 and other features that may be calibrated. Then the system may output an indication of the sample (Step 360) that may identify a microbe in the sample, identify a disease the patient has that gave the sample, or other indications.

Example 2: Valve Based Connectors

Figures 4A, 4B:
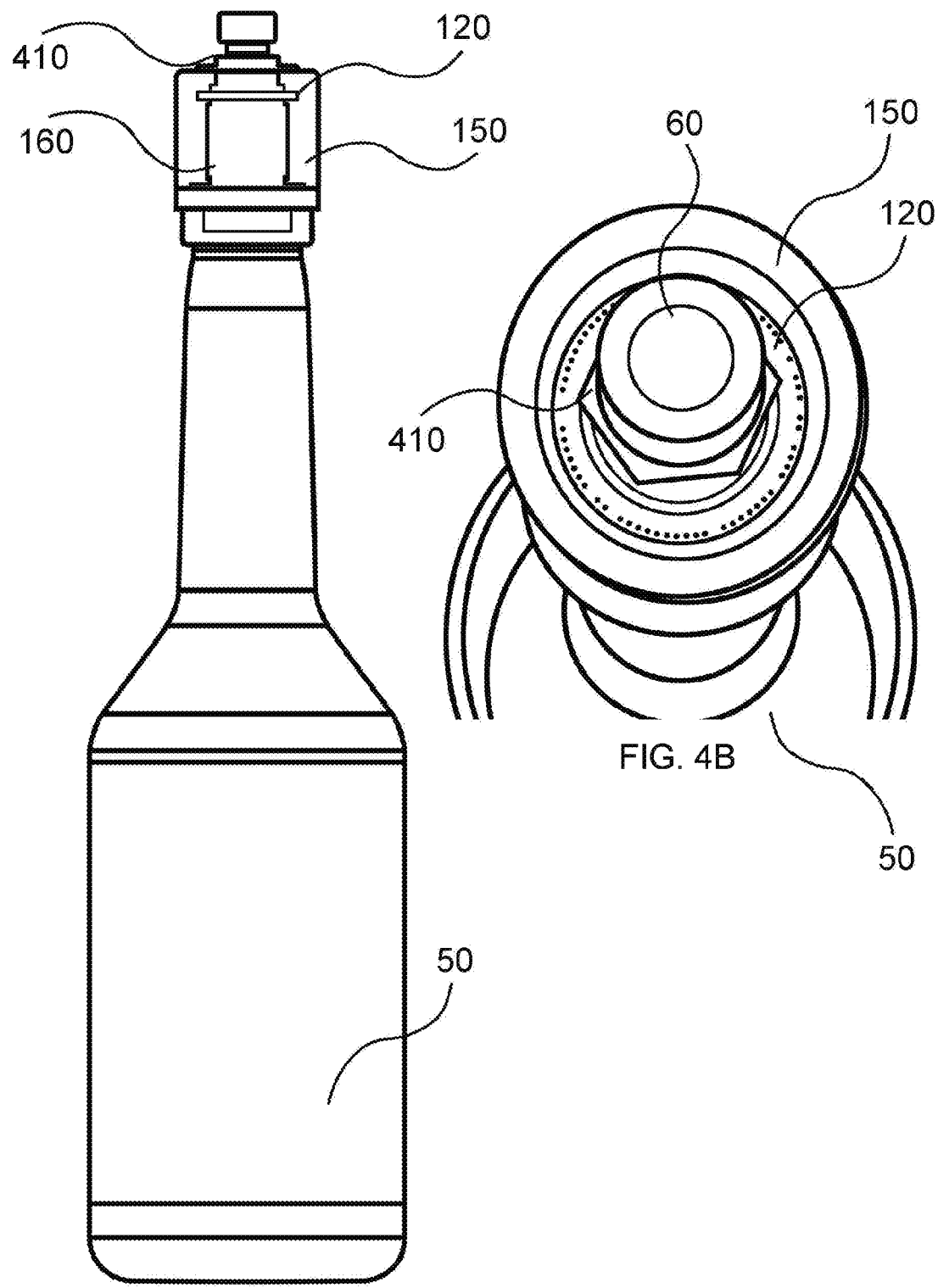
FIG. 4A depicts, according to various examples, a side view of a valve based connector attached to a sample bottle.
FIG. 4B depicts, according to various examples, a top view of a valve based connector attached to a sample bottle.

In another example of the present disclosure, valve based connectors 100 may be utilized. In this case, the valve based connectors 100 may connect to a conventional bottle 50 or may connect to a specialized bottle. FIG. 4A illustrates an example of a valve based connector 100 that is constructed in accordance with the principles of the present disclosure. In this example, the valve based connector 100 includes a compartment 150, a colorimetric sensor array 120 in the form of a ring, and a knob 410 connected to a valve 160 system. The knob 410 may be any dial, knob, or other actuator connected to a moveable portion of the valve 160 system integrated in the connector 100 that moves a portion of the valve 160 to open and close it. The valve system 160 when opened will form a path from the headspace gas of the bottle 50 to the compartment 150 of the CSA 120.

FIG. 4B illustrates an example of a top down view of this valve embodiment of the connector 100 that includes a septum 60 and a clear view of the CSA 120 that is constructed in accordance with the principles of the present disclosure. In this example, the user may inject the sample with a needle through the septum 60. Then, the user may open the valve by turning the knob 410 at any time. In some examples, a certain time will be specified, or the valve will be turned as soon as possible for consistent results.

Figure 5:
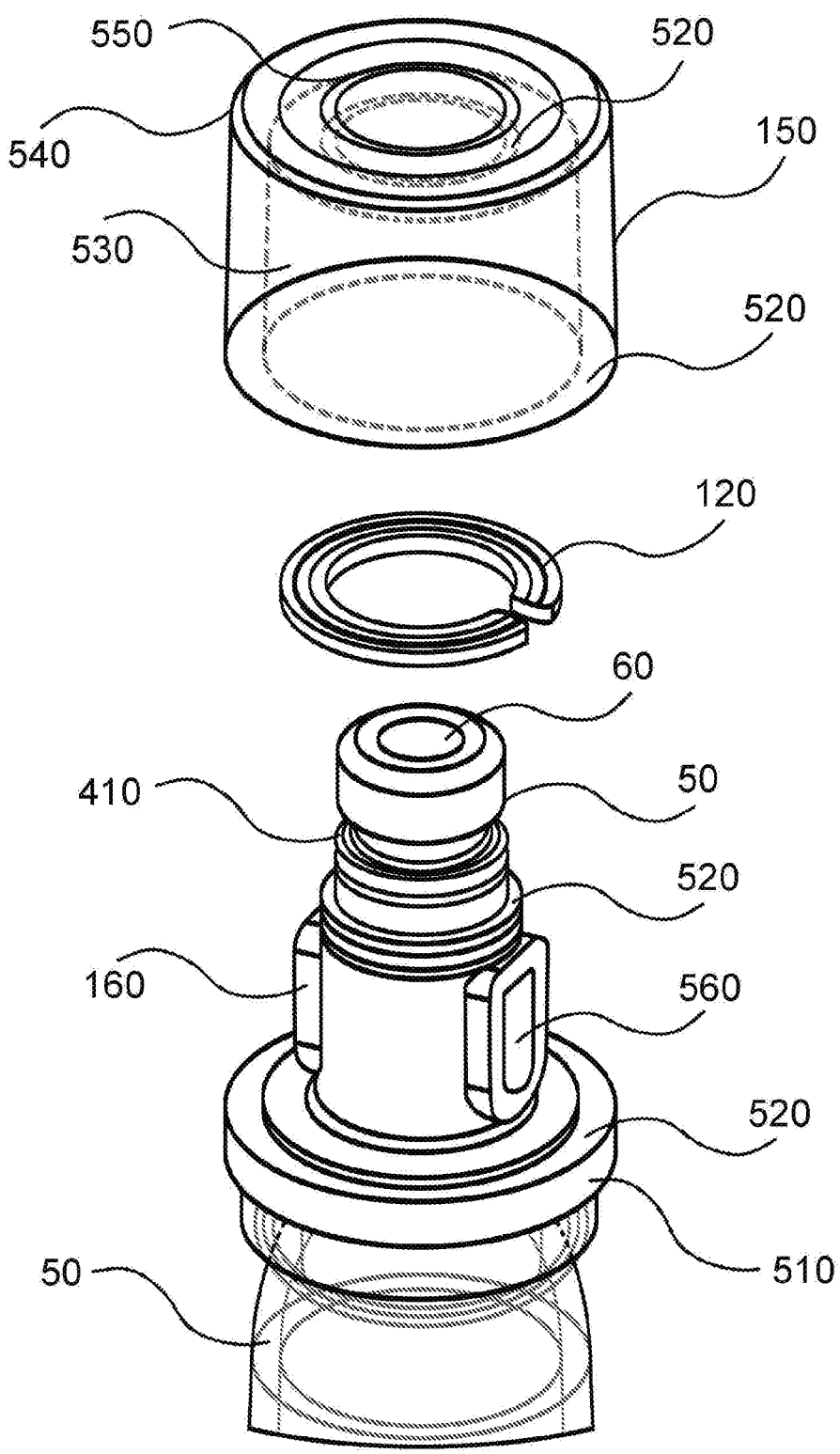
FIG. 5 depicts, according to various examples, an exploded view of a valve based connector attached to a sample bottle.

FIG. 5 illustrates a perspective and exploded view of this example of a valve based connector 100. The connector 100 includes a retainer 510 that may be a plug or press fit tab that fits within the opening of the bottle 50. The connector 100 is illustrated with the compartment 150 or cap removed that fits over the connector 100 and is welded or sealed on seams 520. Those seams 520 form an airtight fit over the rest of the connector 100 including the CSA 120 after the CSA 120 is attached to the connector 100.

For instance, in some examples, the CSA 120 will be attached to the connector 120 after autoclaving the connector 100 and bottle 50, and then the compartment 150 or cap can be sealed to the seams 520. This will allow the majority of the system to be autoclaved except for the CSA 120 which may not survive the sterilization process in some examples. In other examples, the CSA 120 may be contained within the compartment 150, and the compartment and CSA 120 may be attached to the rest of the connector 100 at the same time.

FIG. 5 also illustrates the external valve ports 560 of the valve system 160. Once the valve 160 is opened, headspace gas from the bottle 50 can diffuse through the conduits and exit the external valve port 560 and enter the compartment 150 and come into contact with the CSA 120.

As illustrated, to open the valve system 160, a valve knob 410 is included that may come in a variety of forms. For instance, the valve knob 410 may be nut shaped, or have other features that allow only a tool to be inserted in the top opening 550 of compartment 150 to rotate or actuate the knob 510 and in turn opening the valve 160 system. In other examples, the knob 410 may be a lever, or other actuation device. The seals 520 may be any suitable seals to form an airtight barrier to maintain a gas tight environment inside the compartment 150 with CSA 120.

FIGS. 6A-6B illustrate an example of a CSA 120 that is ring shaped, with an opening to allow for the CSA 120 to be wrapped around the valve or other portion of the connector 100. In other examples, the ring shaped CSA 120 may not have a gap and may instead be fit over the top and slid into place. The CSA 120 may not have a hole in the center and could be contained in the top portion of the compartment 150, could be square, rectangle, or other suitable shapes.

In some examples, the CSA includes a top portion with chemoresponsive dyes printed on a substrate, and a bottom support ring 610 that has the structure properties to retain the CSA 120 in place. For instance, support ring 610 may be made of a retention plastic that holds its shape or other elastic material that can be wrapped around the valve 160 system to hold it into place.

Figure 7A:
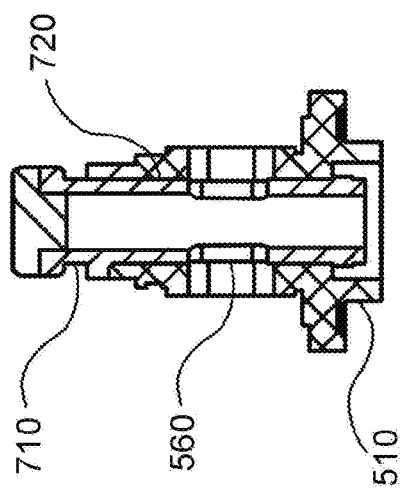
FIGS. 7A-7B depict, according to various examples, perspective view of a valve for a connector.
Figure 7B:
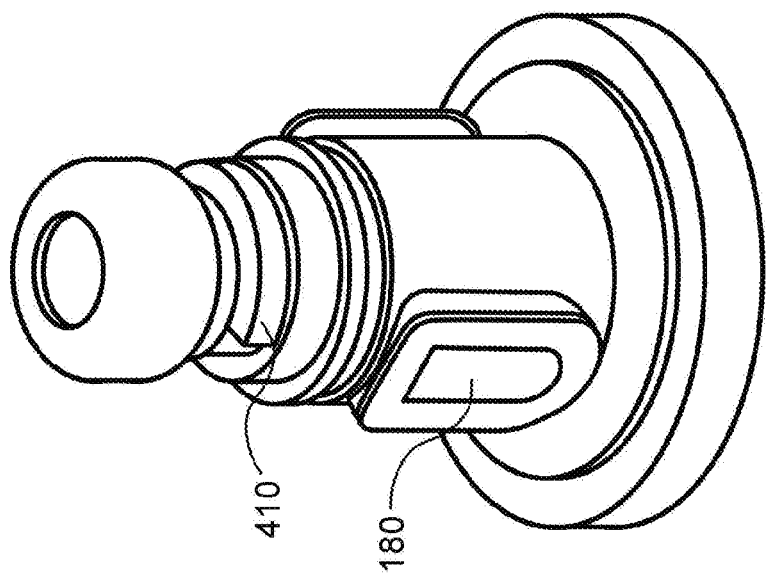
Figure 7C:
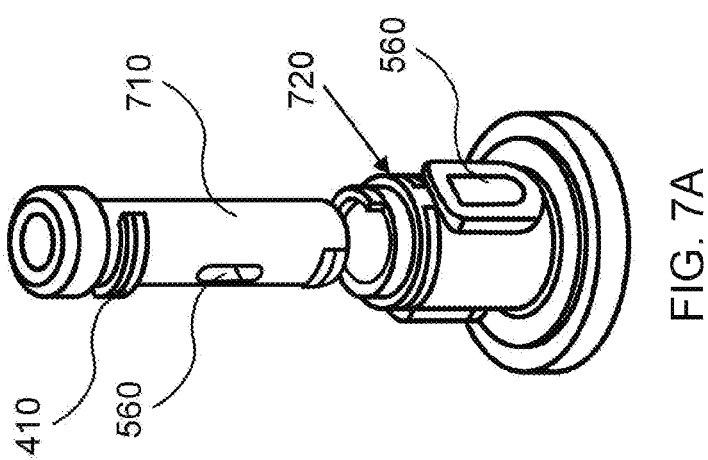
FIG. 7C depicts, according to various examples, a longitudinal cross sectional view of a valve for a connector.

FIGS. 7A-7C illustrate perspective views of the valve system 160 of this example. Referring to FIGS. 5 and 7A together, the valve system 160 includes an inner valve 710 that may be rotated into place by actuating or rotating the knob 410 with a tool. In this example, inner valve 710 includes an inner valve port 560 that may be lined up with external valve port 560 on output valve 720 to open the valve system 160 and allow gas to flow.

FIG. 7C illustrates a cross sectional view of the valve system 160. In this example, the inner and outer valve ports 560 are lined up to form a channel that can conduct gas from the bottom of the valve system through a conduit in the center of inner valve 710 and out out through valve ports 560 to enter compartment 150 and contact CSA 120. FIG. 7C also illustrates a retainer 510 that may be inserted into the mouth or opening of a bottle 50. In some examples, the retainer 510 may be a press or friction fit into the bottle 50.

FIG. 7B also illustrates an example of a filter 180 that may be a biofilter as disclosed herein and/or a hydrophobic filter to keep liquid or other sample related contaminants out of compartment 150 and from contacting CSA 120.

FIGS. 8A-8B illustrate an example of the valve system 160 (as shown in, e.g., FIG. 5) when the valve system 160 is closed and does not allow VOCs or other gasses to exit through valve ports 560. FIG. 8A shows a cross sectional view of the inner valve 710 and outer valve 720 with the valve ports 560 not lined up. FIG. 8B illustrates a longitudinal cross sectional view and illustrates the flow path of VOCs that cannot exit the valve system 160 because the valve 160 is closed.

FIGS. 9A-9B illustrate an example of a valve system 160 (as shown in, e.g., FIG. 5) where the valve has been opened by rotating the inner (or the outer) valve 710 so that the valve ports 560 line up and open the channel as shown in FIG. 9A. In other examples, the valve 160 may be opened by rotating a sleeve surrounding a valve 160, by pushing an inner valve 710 or outer valve 720 up or down to line up the valve ports 560, or other suitable means of opening a valve mechanically. In other examples, a simple electronic valve may be included.

FIGS. 10A-10C illustrate further embodiments of the outer valve 720 portion of the valve system 160 (as shown in, e.g., FIG. 5). In these examples, illustrated are the ports 560, and the filter 180. In other examples, there may be multiple filters 180. For instance, there may be filters 180 on the bottom portion that block liquid (e.g. hydrophobic) and filters 180 on the inside or outside of the valve ports 560 and on the inner or outer valve ports 560.

FIGS. 11A-11B illustrate examples of inner valve 710 that is constructed in accordance with the principles of the present disclosure. In this example, inner valve 710 may include a cap 50 and septum 60. The inner valve 710 here contains a conduit through the entire center of the inner valve 710. This conduit will allow access through the septum 60 to deposit a sample in a connected bottle 50. Additionally the conduit allows VOCs to flow from the sample bottle 50 out through the valve ports 560. In other examples the inner valve 710 may be rectangular and allow for up and down motion (instead of rotation) to line up the valves.

FIGS. 12A-12B illustrate an example of another rotary valve system that includes a knob 710 (as shown in, e.g., FIGS. 7A-7B) in the form of a nut. In this example, the nut requires a special tool to rotate the inner valve 710 to open and line up the valve ports 560 of inner valve 710 and outer valve 720. In this example, the compartment 150 is constructed as a donut or ring shape that allows a small space between the compartment 150 and knob 710. This allows the knob 710 to be recessed within the space in the middle of the compartment to only allow a thin tool to be inserted to rotate knob and inner valve 710 to open the system. In other examples, the knob 710 may have a recess for a screw driver or other tool to rotate the knob. Illustrated additionally is CSA 120 inside of compartment 150 with a transparent or nearly transparent window on top of the compartment 150.

Figure 13:
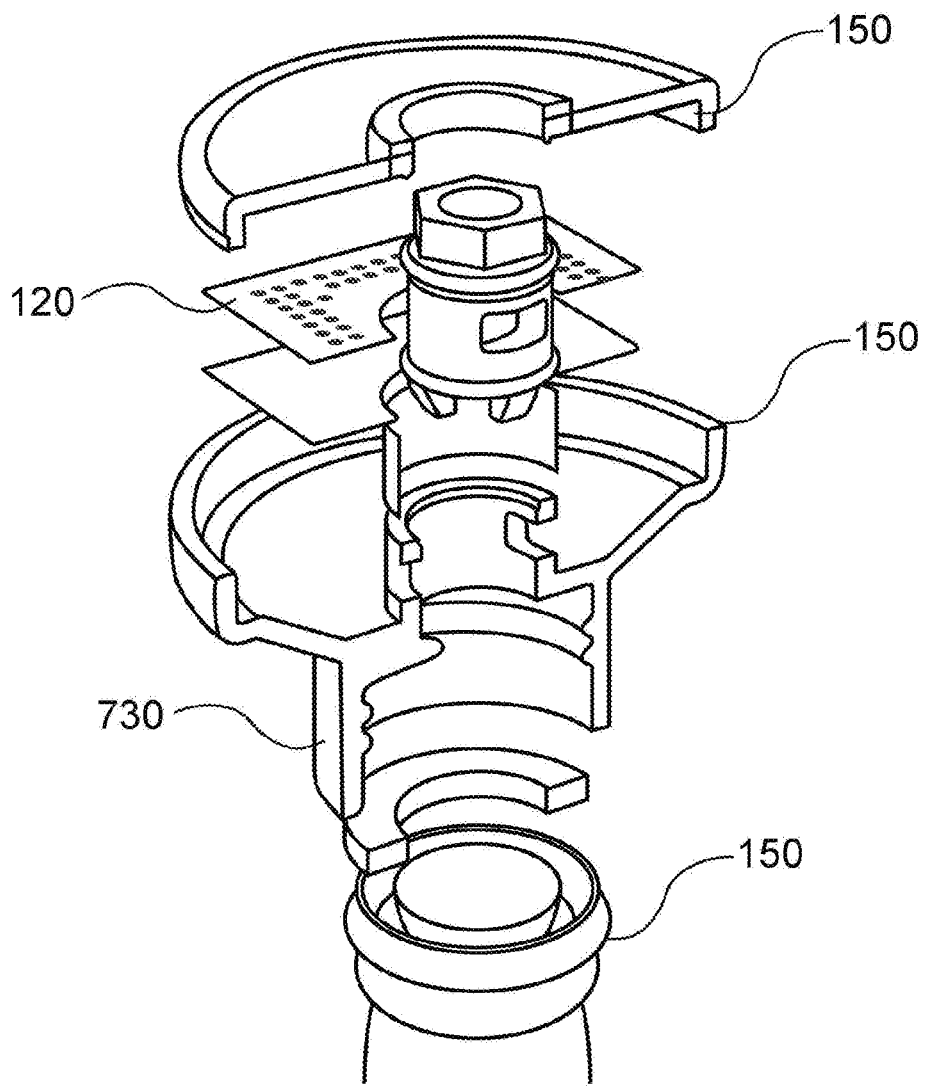
FIG. 13 depicts, according to various examples, an exploded cross-sectional view of a valve based connector attached to a sample bottle.

FIG. 13 illustrates an exploded, cross sectional view of the connector 100 that includes a disc rotating valve 150. In this example, a retainer 730 is illustrated that includes a screw on retainer 730 with a gasket to seal the connector to the bottle 50 top. Other retainers 730 may be utilized as disclosed herein. As illustrated, compartment 150 may include a top half that is transparent for detection, and a bottom half that is opaque.

Figure 14:
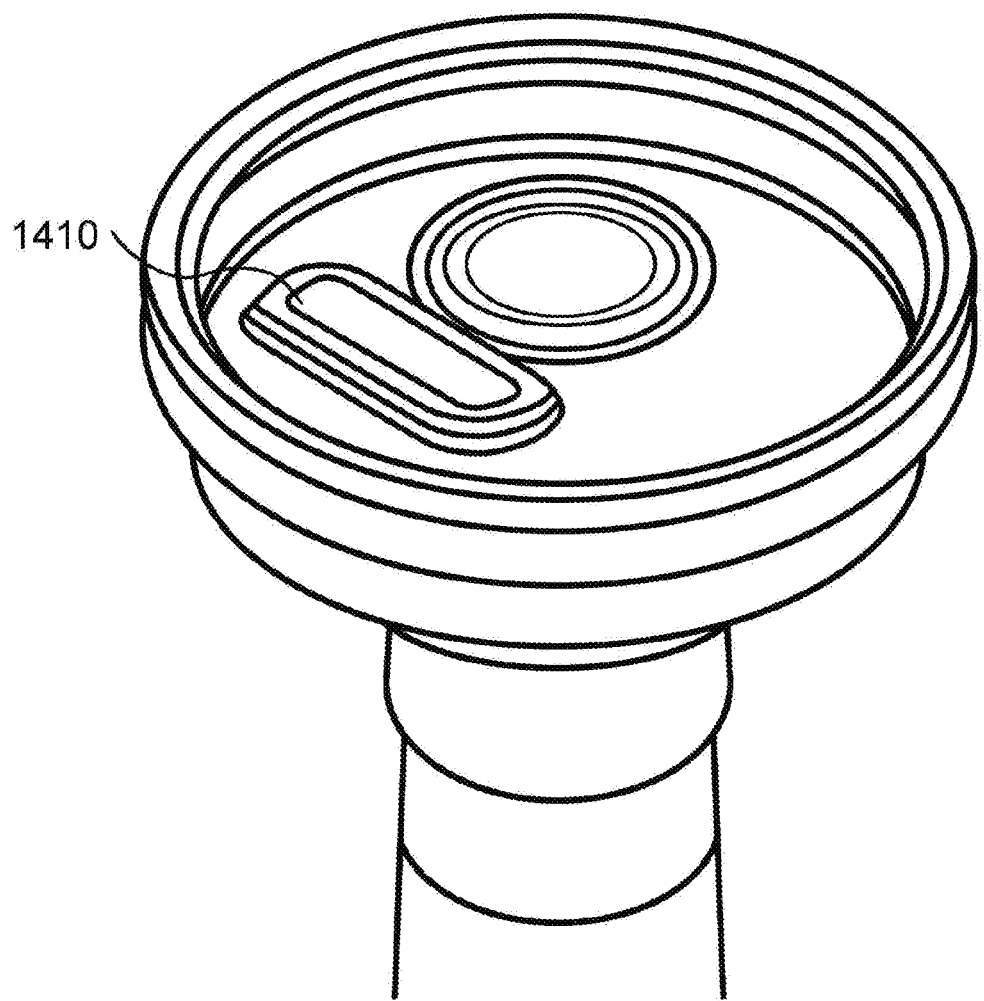
FIG. 14 depicts, according to various examples, a perspective view of a valve based connector attached to a sample bottle.

FIG. 14 illustrates an example of a valve based connector 100 that includes a valve 710 that may be pushed in (or retracted) to line up the valve port 560 as illustrated in FIGS. 15A-15B. In other examples, the inner valve 710 may be pulled out to line up the channels, or rotated in a different plane. In some example, the inner valve 710 may be slide horizontally instead of vertically to line up ports 560.

FIG. 16 illustrates another example of a valve based connector 100 that includes a CSA 120 and an inner valve 710 that may be rotated in a horizontal plane to open a port 560 to release gas to contact the CSA 120. In other examples, inner valve 710 may be pulled up or pushed down vertically to line up internal ports 560.

FIGS. 17A-17C illustrate a perspective cross sectional view of an example connector 100 that uses a combination septum 60 with inner valve 710. In this example, the septum 60 may both provide access to deposit a sample in a bottle with a needle and also provide an inner valve 710 that may be retracted or pushed down vertically in this example, to line up valve ports 560. In this example, the inner valve 710 may be pulled out using a tool, such as a cork screw like device or a hook. Or in some examples, the inner valve 710 may include a pull tab or space to be pushed downward.

FIGS. 17A-17C also illustrate an example of a retainer 185 that is a clip on with a gasket. This is advantageous because it does not require a screw system and a special bottle 50 but potentially could be attached to convention bottles 50 once a cap 60 is removed.

Figure 18:
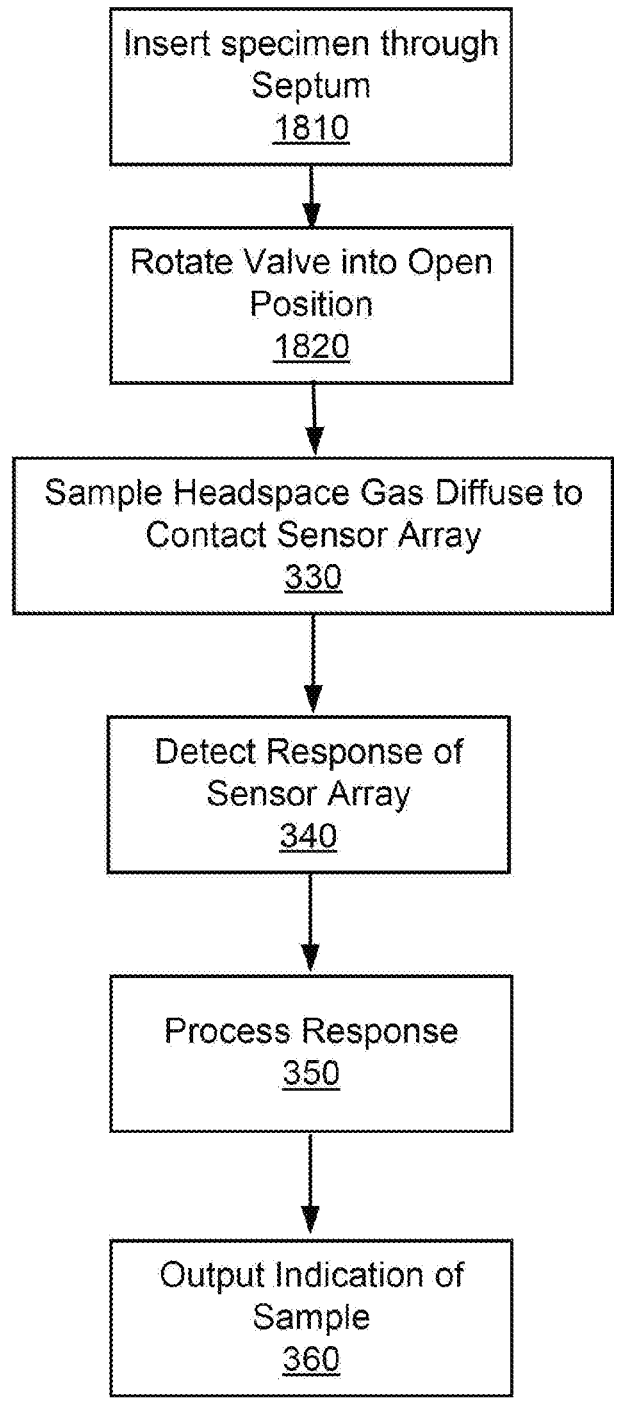
FIG. 18 depicts, according to various examples, a flow chart illustrating a method of using a valve based connector.

FIG. 18 illustrates an example method of using the valve based connectors 100. For instance, first the specimen may be inserted through the septum 1810, as many of the valve based connectors 100 (but not all) may include a septum. In many examples, this will be the case and this will allow the valve system to be pre-attached to the bottle 50 prior to introduction of the sample.

Accordingly, a technician only needs to rotate the valve into position 1820 to open the valve system 160. This is advantageous because there is smaller room for error or variability and requires less instructions than, for example, a needle based connector 100 that must puncture a septum and be clipped onto the bottle 50.

Then, the user will allow the sample headspace gas to diffuse to contact the sensor array 330 through the valve ports 560. While this is happening, a detector will be detecting the response of the sensor array 340. Then, a control system may process the response of the detector 350. In some examples, the control system may include different processing criteria based on the model of the connector 100. For instance, each connector 100 may include different diffusion rates, transmission characteristics through the window of the compartment 150 and other features that may be calibrated. Then the system may output an indication of the sample 360 that may identify a microbe in the sample, identify a disease the patient has that gave the sample, or other indications.

Example 3: Seal Breaking Connectors

FIGS. 19A-19B illustrate examples of connectors that are configured to break seals 1920 internally to allow the headspace gas to flow to the CSA 120. For instance, in some examples, a connector 100 may contain at least one protrusion 1920 that may be advanced to penetrate and break the seal 1920. The protrusion 1910 may include a spike, a rectangular or cylindrical tab, a spear, or other suitable mechanisms for piercing and opening a seal 1920. In some examples, the protrusion 1910 may have a blunt end to ensure the seal 1920 is completely punctured and not just opened.

In some examples, the seal 1920 may be a breakable plastic membrane, a metal membrane, a foil with plastic backing, or other material. Seal 1920 will have to be airtight to avoid transmission of VOCs or other microbes or contaminants until seal 1920 is broken to avoid contamination of the CSA 120.

FIGS. 19A-19B illustrate one example of how a seal may be broken, for instance in this case the connector 100 includes a screw retainer 185, and the screw portion may be further twisted to advance the protrusion 1910 towards the seal 1920 to ultimately puncture the seal 1920 as illustrated in FIG. 19B. The advantages of this system and method are that the internal passageways do not move and therefore it may be less complex to manufacture. However, it is not certain if breaking the seal will result in uniform breakage, and therefore materials may be chosen that completely shatter and open the passageway.

Figure 20:
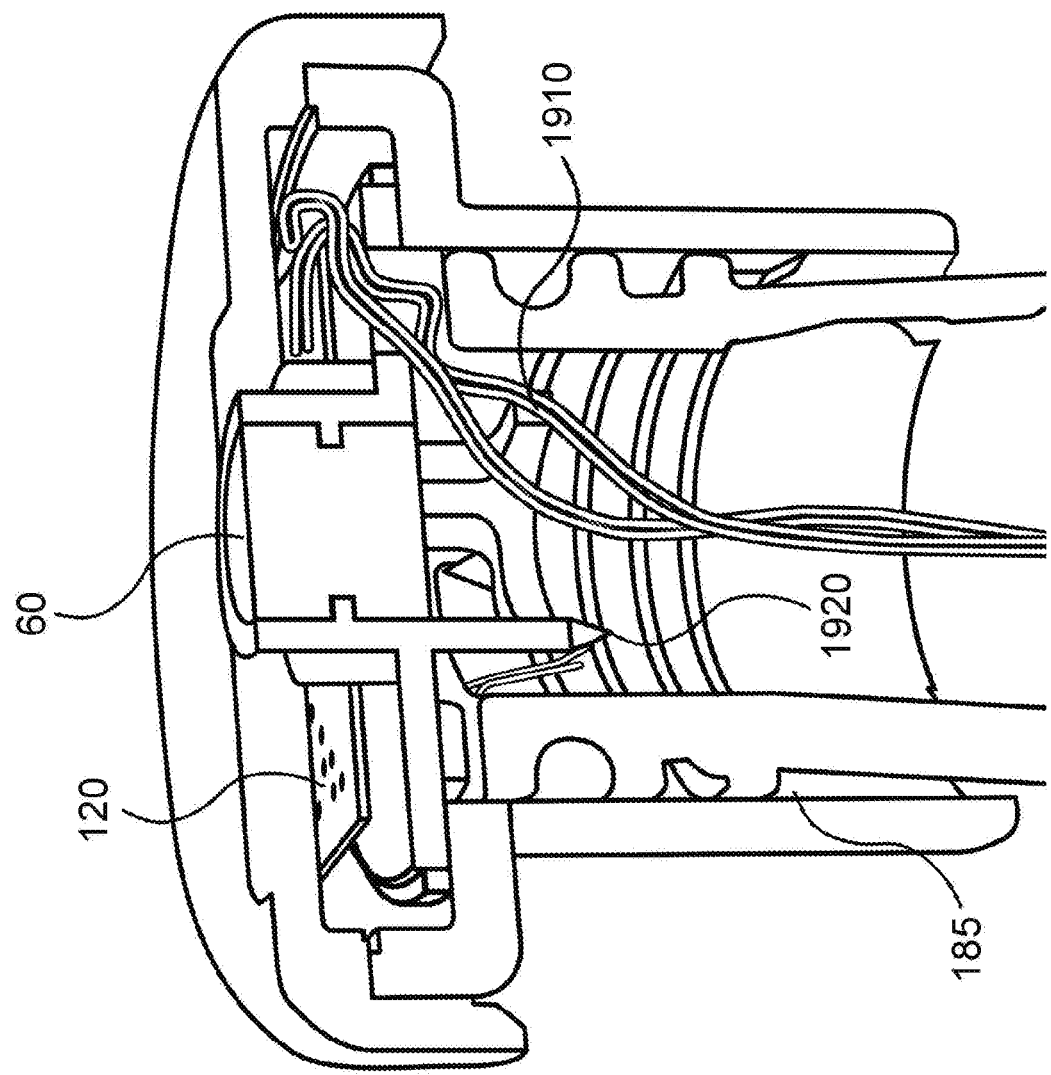
FIG. 20 depicts, according to various examples, a perspective cross sectional view of a seal breaking based connector attached to a sample bottle.

FIG. 20 illustrates another embodiment that requires the user, or an automated device to push down on the connector which breaks the seal 1920. In this case, a ribbed portion of retainer 185 clips behind ridges on the bottle 50 once the connector 100 is pushed downward. Then stops will prevent further downward motion of the connector once seal 1920 is pierced.

Figure 21:
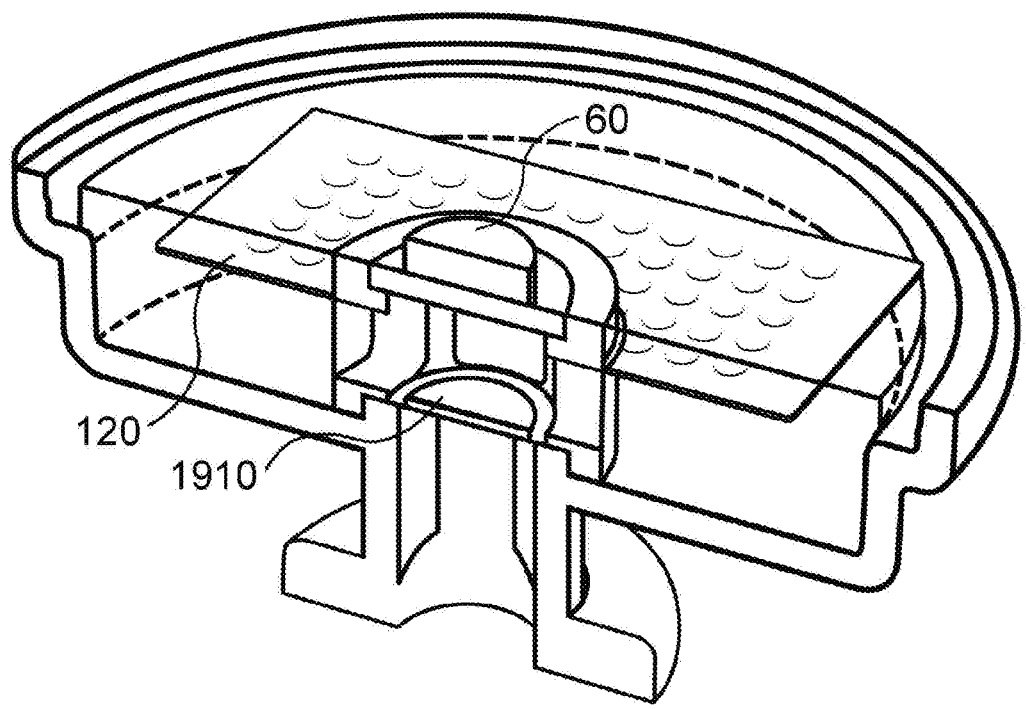
FIG. 21 depicts, according to various examples, a perspective cross sectional view of a seal breaking based connector.

FIG. 21 illustrates a perspective and cross sectional view of a connector 100 that includes a seal 1910 that is breakable by insertion of a needle or other device through septum 60. The seal 1920 in this case may be made so that the seal breaks away completely by introduction of a needle, and it does not just pierce it. This system may be advantageous, because as soon as the sample is delivered with the needle into the bottle, the seal 1910 will be broken and diffusion can take place immediately. This also greatly simplifies the process, so the operator only has to perform one action to deposit the sample and break the seal.

Figure 22A:
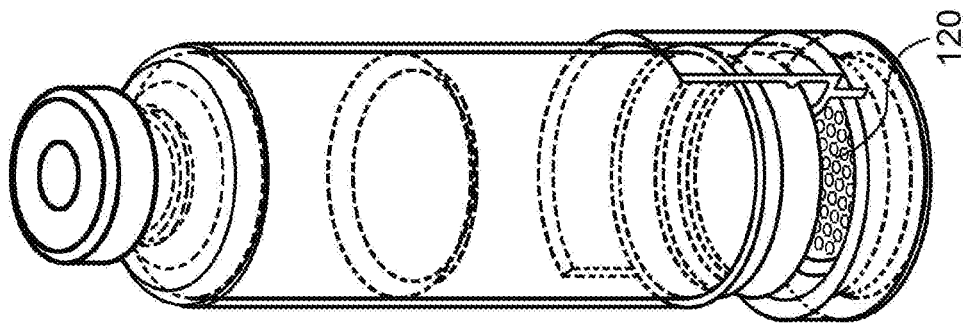
FIGS. 22A-22B depict, according to various examples, longitudinal cross sectional views of seal breaking based connectors attached to a sample bottle.
Figure 22B:
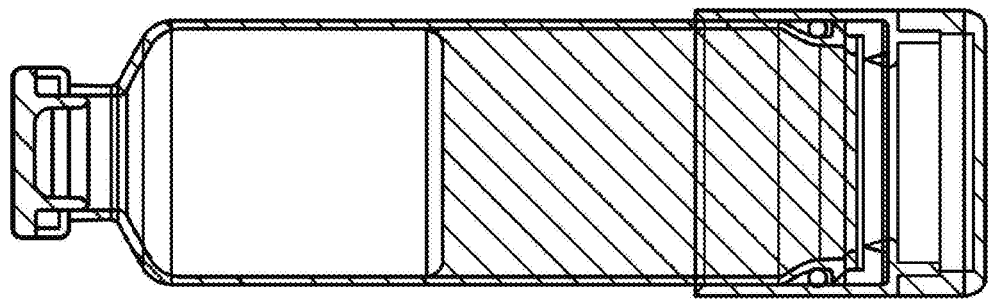
Figure 22C:
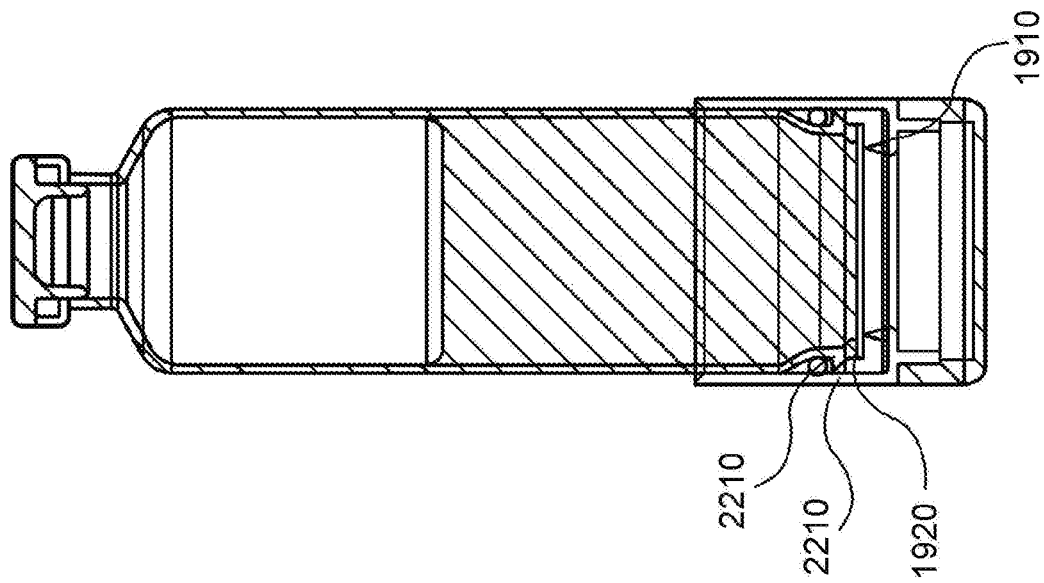
FIG. 22C depicts, according to various examples, a perspective view of a seal breaking based connector attached to a sample bottle.

FIGS. 22A-22C illustrate cross sectional (and 22C perspective) views of another embodiment of a connector 100 that includes a breakable seal. In this example, the bottle includes tabs 1920 that initially retain bottle and sample portion in an elevated position. Then, the user can push down and protrusions 1910 may break the seal 1920 and allow the headspace gas to pass through the seal 1910 area and contact the 120 CSA. The user can push the bottle down until the tabs snap into a locked position as show in FIG. 22B. In some examples, the bottle 50 or connector 100 will contain a hydrophobic membrane that is prevents liquid or sample from contacting the seal 1910 or advancing through the seal 1910 but will allow the VOCs to pass through to the CSA 120.

Figures 23A, 23B:
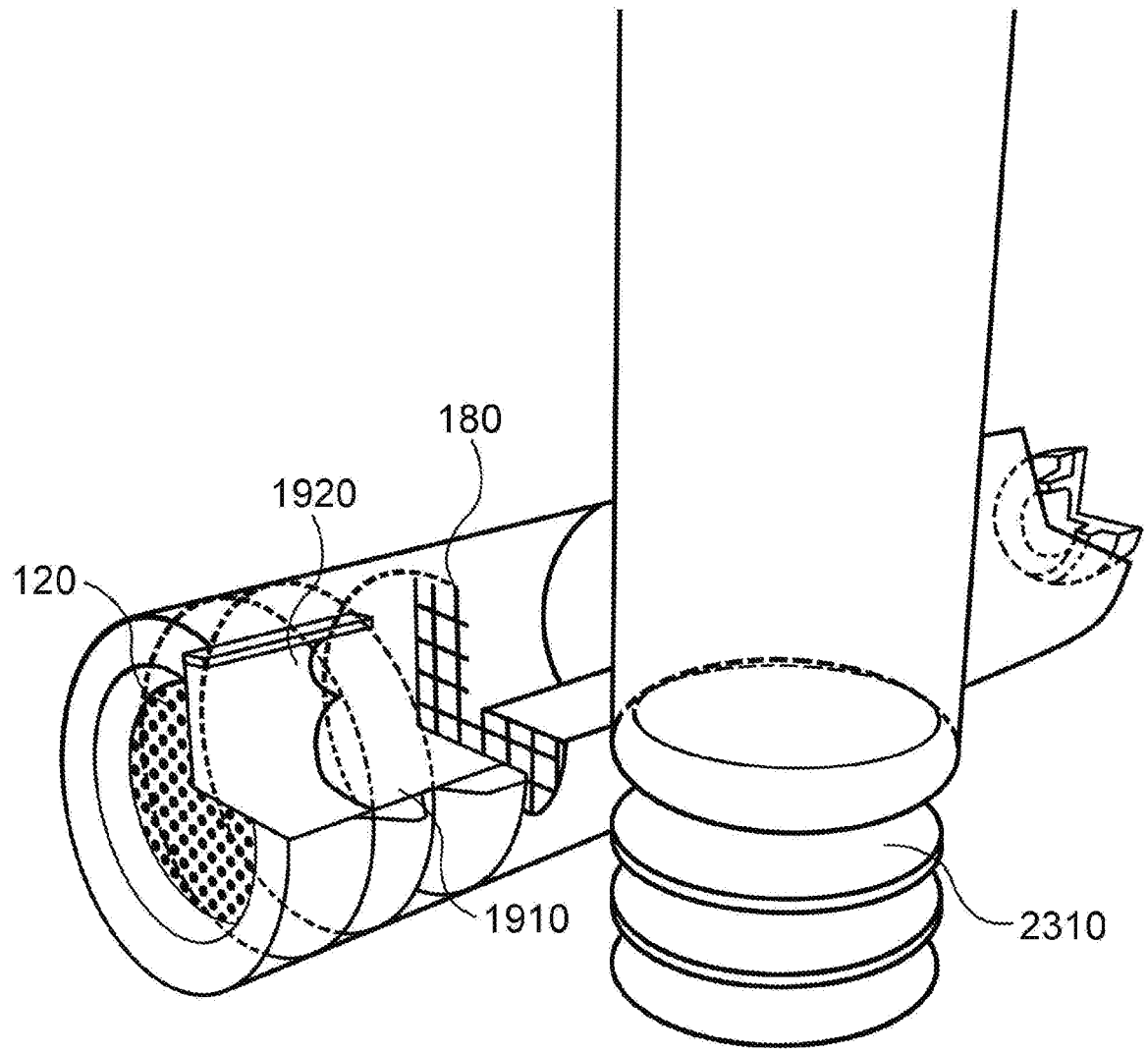
FIG. 23A depicts, according to various examples, a perspective cut out view of a seal breaking based connector attached to a sample bottle.
FIG. 23B depicts, according to various examples, a perspective view of a seal breaking based connector attached to a sample bottle.

FIGS. 23A-23B illustrate an example of a connector 100 with a breakable seal 120 that includes protrusions 1920 that are directed towards seal 1910. Additionally, the connector also includes filter 180 that may be a hydrophobic filter to prevent sample or sample medium from crossing and only allowing gas to pass through. In other examples, where the sample is gas, the filter 180 may only be a biofilter 180 that allows VOCs to pass. In other examples, there may be combinations of filters 180.

FIGS. 23A-23B also illustrate a bellows 2310 structure that allows the connector to be compressed in order to advance the protrusions 1920 into the seal 1910 in order to break the seal 1910. The bellows structure allows movement without compromising the isolated nature of the bottle 50.

Figure 24:
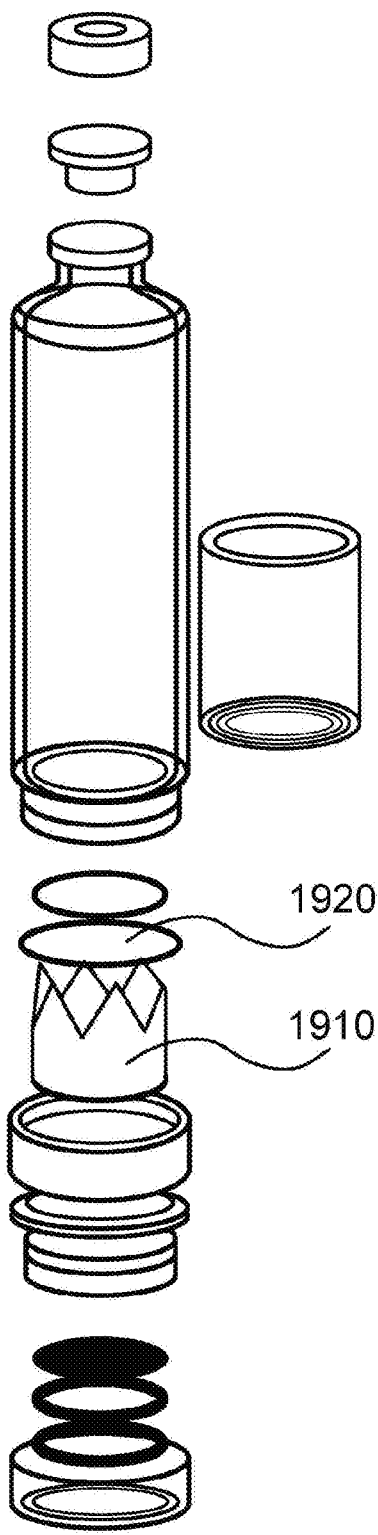
FIG. 24 depicts, according to various examples, an exploded view of a seal breaking based connector attached to a sample bottle.

FIG. 24 illustrates an exploded view of the bellows embodiment, including examples of the components that could be used, including the protrusion/crown disk 1910. In other examples, the protrusions 1910 could have spikes or other structures.

Figure 25:
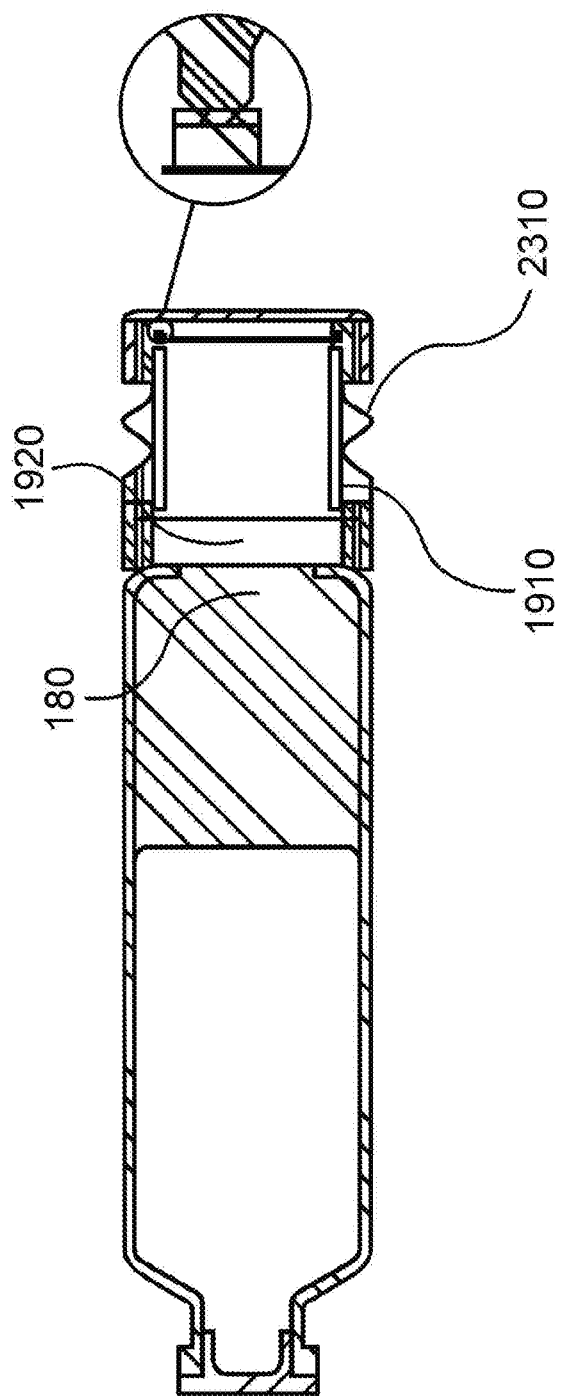
FIG. 25 depicts, according to various examples, a cross sectional view of a seal breaking based connector attached to a sample bottle.

FIG. 25 illustrates a cross sectional view of a bellows embodiment that shows the bellows 2310, and the protrusions 1910, seal 1920 and a filter 180. Accordingly, the wet and sterile area remains on the bottle 50 side of the filter 180, in examples where the sample or medium include liquid. In other examples, filter 180 may be a biofilter 180 and separate out only VOCs.

Figure 26:
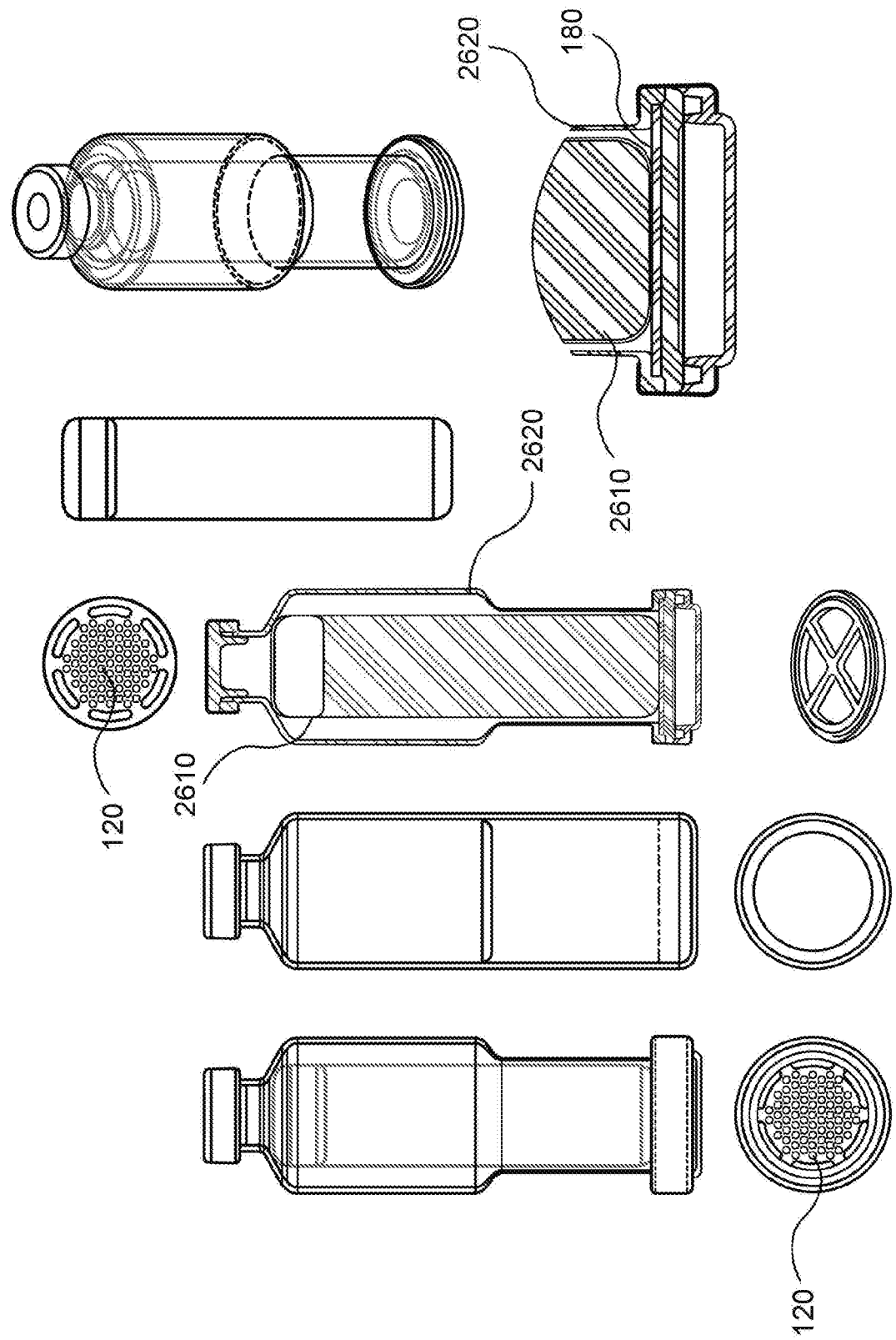
FIG. 26 depicts, according to various examples, cross sectional views and perspective views of various ampoule based breakable sample bottles with connectors.

FIG. 26 illustrates an example of a glass ampoule based embodiment that includes a plastic or other flexible outer casing 2620 and a breakable barrier 2610. Accordingly, this would allow a user or a machine to break the glass ampoule by squeezing or manipulating the flexible barrier 2620. This would allow the liquid sample to contact a filter (e.g. hydrophobic barrier) that would allow gas to pass through the filter 180.

Figure 27:
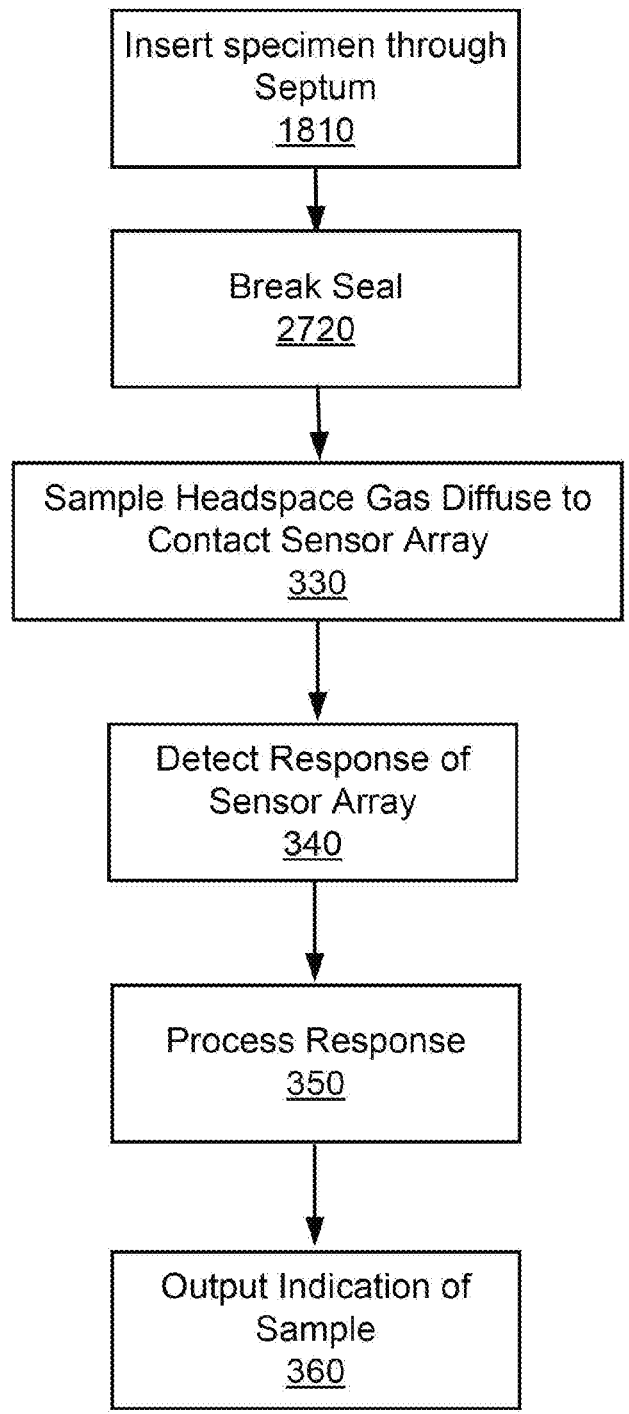
FIG. 27 depicts, according to various examples, a flow chart illustrating a method of using a seal breaking based connector.

FIG. 27 illustrates an example method of using a connector 100 that includes a breakable seal or other breakable portion. In some examples, this includes inserting the specimen through the septum (Step 1810), or in some examples, the sample may be pre-inserted prior to adding the connector. However, in this embodiment, the bottle 50 may be prefabricated to include the connector 100 in some examples.

Next the user or clinician would break the seal (Step 2720), or in some examples an automated process may break the seal for instance, an incubator or other automated mechanism may apply pressure so the seal breaks.

Then, the technician will allow the sample headspace gas to diffuse to contact the sensor array (Step 330) through the valve ports 560. While this is happening a detector will be detecting the response of the sensor array 340. Then, a control system may process the response of the detector 350. In some examples, the control system may include different processing criteria based on the model of the connector 100. For instance, each connector 100 may include different diffusion rates, transmission characteristics through the window of the compartment 150 and other features that may be calibrated. Then the system may output an indication of the sample 360 that may identify a microbe in the sample, identify a disease the patient has that gave the sample, or other indications.

Example 4: Seal Removal Connectors

Figure 28:
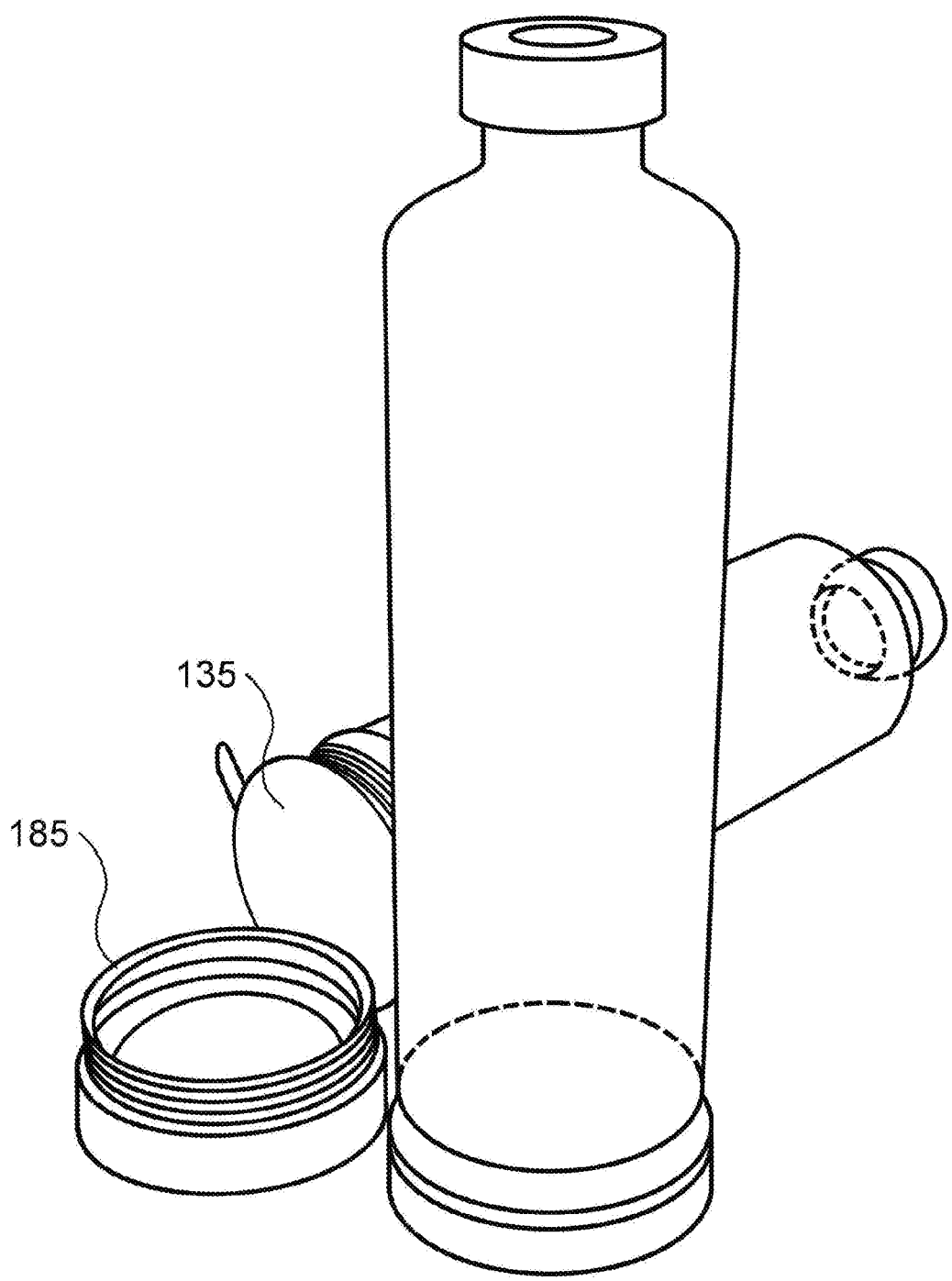
FIG. 28 depicts, according to various examples, a perspective view of a seal based connector attached to a sample bottle.

FIG. 28 illustrates an example of a connector 100 that includes a screw based retainer 185 that is applied after a seal 135 is removed from the bottle 100 that would allow the VOCs to exit the bottle 50 through a filter 180 once it is removed. This model is advantageous is that it uses a simple system, but introduces some oxygen into the process once the seal is removed from the bottle. Accordingly, this system does not remain a closed system throughout.

Figure 29A:
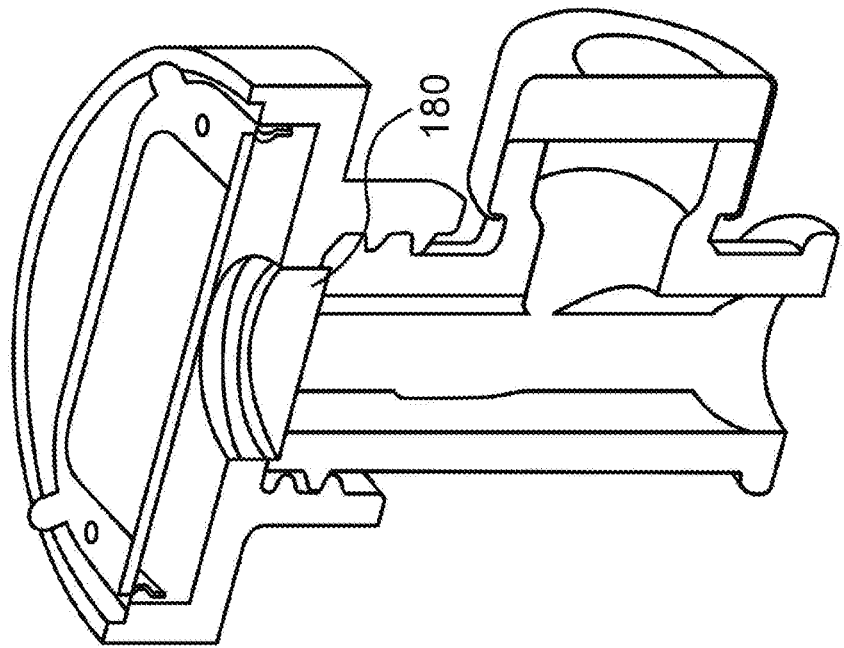
FIG. 29A depicts, according to various examples, a perspective cross sectional view of a T junction based sample bottle.
Figure 29B:
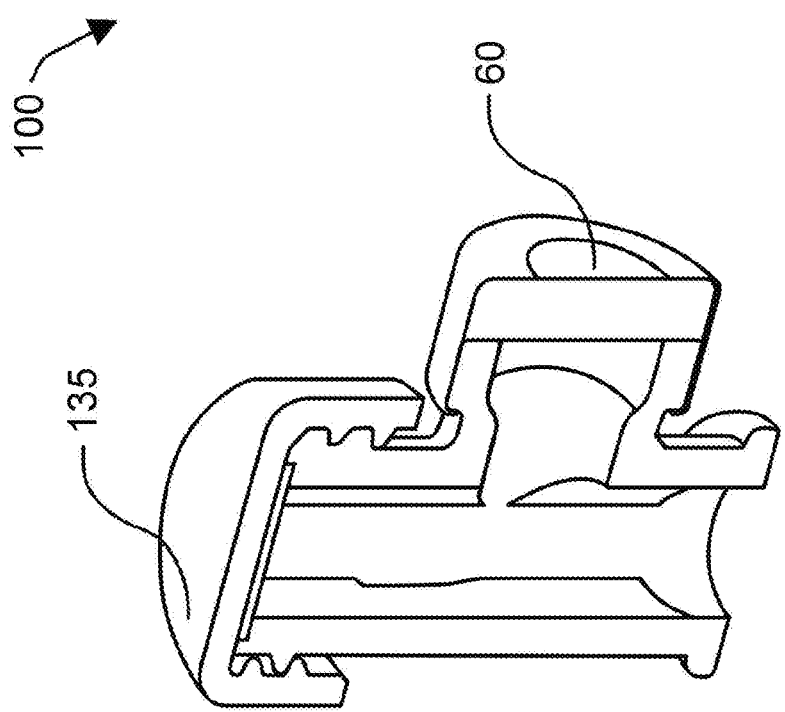
FIG. 29B depicts, according to various examples, a perspective cross sectional view of a T junction based sample bottle with a connector.

FIGS. 29A-29B illustrates an example of a T shaped connector that includes a screw off cap 135 on one side that covers a filter 180 (e.g. hydrophobic gas permeable filter). Once the cap 135 is removed the connector 100 may be screwed onto, clipped on, or use other retainers as disclosed herein. This model also has the disadvantage of allowing existing headspace gases to escape and also allowing ambient gases into the system once the screw is removed. This model also includes a cap and septum 60. In other examples, the shape of the branches may form a Y to allow easier access for a needle to retrieve sample by entering through the septum 60. In other embodiments, the cap and septum 60 may be on the top to allow easy needle access to the sample bottle, and the cap 135, filter 180 and connector 100 may be attached on a side pipe, which only requires diffusion. This embodiment may be advantageous because it does not allow the sample to be deposited through the same shaft as the connector 100 is attached which may reduce contamination.

Figure 30:
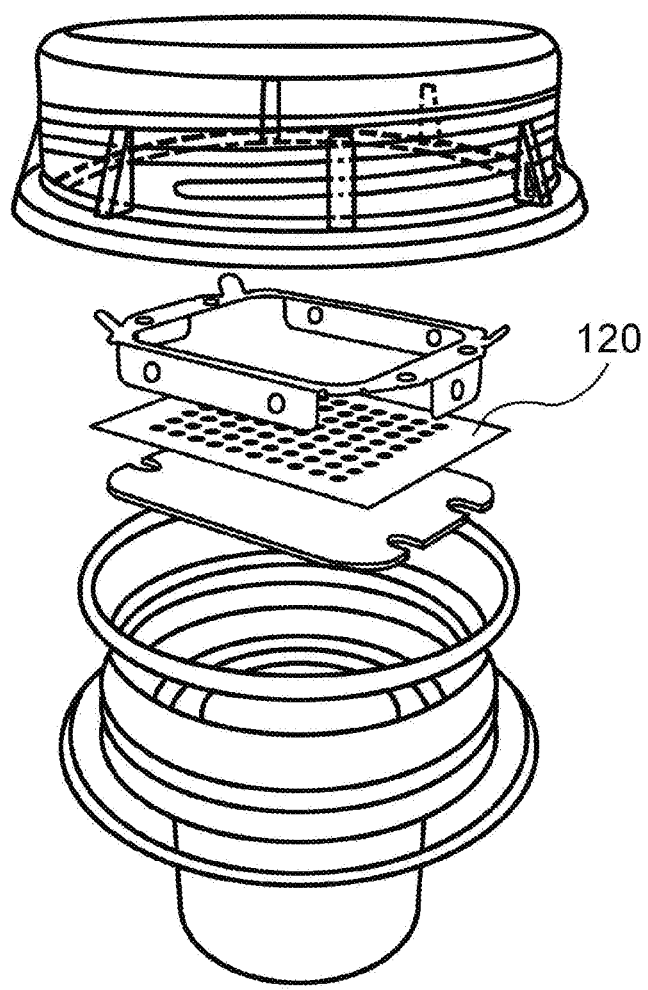
FIG. 30 depicts, according to various examples, an exploded view of a slip on based connector.

FIG. 30 illustrates an example of a slip on connector 100 that has a simple screw together construction. In some examples, the user may simply remove a cap from a bottle 50 and insert the slip on connector 100 into the mouth or neck of the bottle.

SELECTED EMBODIMENTS

Although the above description and the attached claims disclose a number of embodiments of the present invention, other alternative aspects of the invention are disclosed in the following further embodiments.

Embodiment 1

A connector for introducing gaseous particles from a sample bottle to a colorimetric sensor array, the connector comprising:
  a compartment;
  a sensor array inside the compartment, the sensor array comprising at least two chemoresponsive dyes; and
  a needle with a channel connected the compartment, the channel in gaseous communication with the compartment.

Embodiment 2

The connector of embodiment 1, wherein the compartment includes an at least partially transparent window and the sensor array is positioned with the at least two chemoresponsive dyes facing the at least partially transparent window.

Embodiment 3

The connector of embodiment 1, further comprising:
a housing forming a wall on three sides of the needle and a peel away seal covering the fourth side of the needle to form a sterile cavity for the needle.

Embodiment 4

The connector of embodiment 1, sensor array is a colorimetric sensor array.

Embodiment 5

The connector of embodiment 1, further comprising a filter positioned in gaseous communication with the channel of the needle.

Embodiment 6

The connector of embodiment 5, wherein the filter is a hydrophobic filter.

Embodiment 7

The connector of embodiment 5, wherein the filter is a biofilter with pore size of 0.2 um.

Embodiment 8

A method of using the connector of embodiment 1, wherein the needle is plunged through a septum of a sample bottle.

Embodiment 9

The method of embodiment 8, wherein the connector is clipped into the cap of the sample bottle with a retainer attached to the connector.

Embodiment 10

A connector for introducing gaseous particles from a sample bottle to a colorimetric sensor array, the connector comprising:
a compartment;
a sensor array inside the compartment;
a valve comprising at least one valve port in gaseous communication with the compartment;
an actuator connected to the valve; and
a retainer.

Embodiment 11

The connector of embodiment 10, wherein the valve further comprises an inner valve with a valve port and an outer valve with a valve port.

Embodiment 12

The connector of embodiment 10, wherein the actuator is a knob.

Embodiment 13

The connector of embodiment 10, wherein the retainer is a screw assembly.

Embodiment 14

The connector of embodiment 10, wherein the retainer is a clipping mechanism.

Embodiment 15

The connector of embodiment 10, wherein the sensor array is a disc shaped sensor array.

Embodiment 16

The connector of embodiment 10, wherein the inner and outer valve are posited and constructed to allow relative rotation between the inner and outer valve.

Embodiment 17

A method of introducing gaseous particles from a sample bottle to a colorimetric sensor array the method comprising:
providing the connector of embodiment 10;
attaching the connector to a sample bottle; and
manipulating the actuator and thereby opening the valve to allow gas to flow from the sample bottle to the sensor array.

Embodiment 18

The method of embodiment 17, wherein the valve comprises an inner valve with an inner valve port and an outer valve with an outer valve port.

Embodiment 19

The method of embodiment 18, wherein opening the valve comprises lining up the inner valve port and outer valve port.

Embodiment 20

A method of assembling a connector, the method comprising:
attaching the retainer to a sample bottle, the retainer being attached to a valve;
autoclaving the retainer, the sample bottle and valve assembly;
attaching a colorimetric sensor to the valve; and
sealing a compartment onto the valve.

Embodiment 21

A method of using a connector, the method comprising;
providing a connector comprising a compartment with a colorimetric sensor array, the connector attached to a sample bottle with a sample inside;
removing an obstruction from a flow path from the sample bottle gas headspace to the colorimetric sensor array;
detecting a change in the colorimetric sensor array after removing the obstruction; and
processing the change in the colorimetric sensor array to output an indication of the sample.

Embodiment 22

A connector for introducing gaseous particles from a sample bottle to a colorimetric sensor array, the connector comprising:

a compartment;
a sensor array inside the compartment;
a seal blocking a gaseous communication channel between the compartment and a sample bottle;
a retainer; and
a protrusion positioned and configured to be movable to contact and break the seal.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A connector for introducing gaseous particles from a sample bottle to a colorimetric sensor array, the connector comprising:
   a compartment having an opening;
   a sensor array inside the compartment, the sensor array comprising at least two chemoresponsive dyes;
   a needle, protruding from the compartment with a bottom of the needle coupled to the opening of the compartment, the needle having a channel in gaseous communication with the compartment via the opening in the compartment;

at least two retainers surrounding the needle and extending from the compartment in a similar direction as the needle, each of the at least two retainers being an elongated member having a stubbed portion at an extremity of the elongated member, the stubbed portion having a thickness that is greater than a thickness of other portions of the elongated member;

a housing forming a wall around the needle such that the needle and the at least two retainers are located within a cavity formed by the wall; and a peel away seal covering the cavity in which the needle is located, the peel away seal being perpendicular to a major axis of the needle and positioned a distance from a tip of the needle.

2. The connector of claim 1, wherein the compartment comprises an at least partially transparent window, and wherein the sensor array is positioned with the at least two chemoresponsive dyes facing the at least partially transparent window.

3. The connector of claim 1, wherein:
the cavity is a sterile cavity for the needle, the needle being isolated from ambient air.

4. The connector of claim 1, wherein the sensor array is a colorimetric sensor array.

5. The connector of claim 1, further comprising a filter positioned in gaseous communication with the channel of the needle.

6. The connector of claim 5, wherein the filter is a hydrophobic filter.

7. The connector of claim 5, wherein the filter is a biofilter with pore size of 0.2 um.

8. The connector of claim 1, wherein multiple needles protrude from the compartment into the cavity.

9. The container of claim 1, further comprising:
a support ring positioned between an inner surface of the compartment and the sensor array to hold the sensor array in place within the compartment.

10. The connector of claim 9, wherein the sensor array is disk-shaped with the at least two chemoresponsive dyes are arranged in a circular manner around an inner diameter of the disk-shaped sensor array.

11. A method comprising:

removing a seal of a connector from a housing of the connector to expose a needle of the connector, the seal being perpendicular to a major axis of the needle and positioned a distance from a tip of the needle prior to the removing of the seal, and the needle being in a sealed, sterile cavity prior to the removing of the seal; and plunging the tip of the needle of the connector through a septum of a sample bottle such that a channel of the needle is in gaseous communication with a compartment of the connector, the compartment of the connector including a sensor array comprising at least two chemoresponsive dyes; and clipping at least two retainers of the connector onto an underside of a cap of the sample bottle such that the clipped retainers hold the connector attached to the cap of the sample bottle to keep the needle in place, each of the at least two retainers being an elongated member having a stubbed portion at an extremity of the elongated member, the stubbed portion having a thickness that is greater than a thickness of the other portions of the elongated member.

* * * * *